United States Patent
O'Leary et al.

(10) Patent No.: US 11,707,380 B2
(45) Date of Patent: Jul. 25, 2023

(54) EAR APPARATUS AND METHODS OF USE

(71) Applicant: MDIDEAFACTORY, INC., San Diego, CA (US)

(72) Inventors: Michael J. O'Leary, Del Mar, CA (US); Randy Wayland, San Diego, CA (US); Daniel Joseph Braun, San Diego, CA (US); Robert F. Gazdzinski, San Diego, CA (US)

(73) Assignee: MDIDEAFACTORY, INC., San Diego, CA (US)

( * ) Notice: Subject to any disclaimer, the term of this patent is extended or adjusted under 35 U.S.C. 154(b) by 553 days.

(21) Appl. No.: 16/848,730

(22) Filed: Apr. 14, 2020

(65) Prior Publication Data
US 2020/0323684 A1   Oct. 15, 2020

Related U.S. Application Data

(60) Provisional application No. 62/834,283, filed on Apr. 15, 2019.

(51) Int. Cl.
*A61F 7/12*       (2006.01)
*A61F 7/03*       (2006.01)
(Continued)

(52) U.S. Cl.
CPC ............... *A61F 7/12* (2013.01); *A61B 5/163* (2017.08); *A61F 7/007* (2013.01); *A61F 7/0085* (2013.01);
(Continued)

(58) Field of Classification Search
CPC ............. A61B 5/163; A61F 2007/0005; A61F 2007/0059; A61F 2007/006;
(Continued)

(56) References Cited

U.S. PATENT DOCUMENTS

| 4,244,377 A | * | 1/1981 | Grams | A61B 5/4863 |
| | | | | 128/865 |
| 4,408,605 A | * | 10/1983 | Doerr | A61F 11/00 |
| | | | | D24/207 |

(Continued)

FOREIGN PATENT DOCUMENTS

| CN | 204971851 U | 1/2016 |
| WO | WO-2009086649 A1 | 7/2009 |
| WO | WO-2015160196 A1 | 10/2015 |

OTHER PUBLICATIONS

Barros A.C., et al., "From Nystagmus to the Air and Water Caloric Tests," Brazilian journal of otorhinolaryngology, Jan. 2012, vol. 78(4), pp. 120-125.
(Continued)

*Primary Examiner* — Tigist S Demie
(74) *Attorney, Agent, or Firm* — Patent Beach PC

(57) ABSTRACT

Selectively controllable apparatus for insertion into an ear canal, and related methods of use and operation for behavioral control. In one embodiment, the apparatus includes a body configured for insertion into an ear canal. In one variant, the body includes one or more thermal mechanisms which enable selective increase or decrease of temperature of at least portions of the ear canal so as to implement behavioral control of the user, such as to mitigate cravings for food, alcohol, narcotics, or other potentially deleterious substances. In one variant, a mild nausea or pre-nausea condition is created within the user according to a time-temperature profile so as to induce the aforementioned behavioral modification.

17 Claims, 14 Drawing Sheets

(51) Int. Cl.
*A61F 7/00* (2006.01)
*A61B 5/16* (2006.01)

(52) U.S. Cl.
CPC .............. *A61F 7/03* (2013.01); *A61F 7/123* (2013.01); *A61F 2007/0005* (2013.01); *A61F 2007/006* (2013.01); *A61F 2007/0075* (2013.01); *A61F 2007/0078* (2013.01); *A61F 2007/0093* (2013.01); *A61F 2007/0094* (2013.01)

(58) Field of Classification Search
CPC ...... A61F 2007/0063; A61F 2007/0064; A61F 2007/0071; A61F 2007/0075; A61F 2007/0078; A61F 2007/0093; A61F 2007/0094; A61F 7/007; A61F 7/0085; A61F 7/03; A61F 7/032; A61F 7/106; A61F 7/12; A61F 7/123; G06F 2203/04101; G06F 2203/04105; G06F 3/0321; G06F 3/03545; G06F 3/0416; G06F 3/04162; G06F 3/0482; H04L 9/3226; H04L 9/3231; H04W 4/80
See application file for complete search history.

(56) References Cited

U.S. PATENT DOCUMENTS

| | | | |
|---|---|---|---|
| 5,692,059 | A | 11/1997 | Kruger |
| 5,755,681 | A | 5/1998 | Plews |
| 6,082,485 | A | 7/2000 | Smith |
| 6,257,235 | B1 | 7/2001 | Bowen |
| 6,354,296 | B1 | 3/2002 | Baumann et al. |
| 6,543,450 | B1 | 4/2003 | Flynn |
| 7,766,015 | B2 | 8/2010 | Harold et al. |
| 9,088,846 | B2 | 7/2015 | Blanchard |
| 2003/0116165 | A1 | 6/2003 | Huang |
| 2003/0195588 | A1 | 10/2003 | Fischell et al. |
| 2008/0066209 | A1 | 3/2008 | Kayerod |
| 2011/0066172 | A1 | 3/2011 | Silverstein |
| 2011/0158421 | A1 | 6/2011 | Voix et al. |
| 2012/0318605 | A1 | 12/2012 | Brown et al. |
| 2013/0180529 | A1 | 7/2013 | Matich |
| 2013/0247669 | A1 | 9/2013 | Swanson et al. |
| 2013/0296987 | A1 | 11/2013 | Rogers et al. |
| 2014/0062567 | A1 | 3/2014 | Waters et al. |
| 2014/0206947 | A1 | 7/2014 | Isserow et al. |
| 2014/0249608 | A1 | 9/2014 | Rogers |
| 2014/0270257 | A1 | 9/2014 | Bauman et al. |
| 2015/0005793 | A1 | 1/2015 | Collins et al. |
| 2015/0142029 | A1 | 5/2015 | Fahn et al. |
| 2015/0320591 | A1* | 11/2015 | Smith ................... A61F 7/0085 600/407 |
| 2016/0008176 | A1 | 1/2016 | Goldstein |
| 2016/0015098 | A1 | 1/2016 | Conlon |
| 2017/0135854 | A1* | 5/2017 | Rogers ...................... A61F 7/12 |
| 2017/0281416 | A1 | 10/2017 | O'Leary et al. |
| 2019/0001117 | A1 | 1/2019 | Ben-David et al. |

OTHER PUBLICATIONS

Behavior Therapy in Psychiatry, Task Force Report 5. Washington, D.C, American Psychiatric Association, 1973.
Bernstein I.L., "Food Aversion Learning: A Risk Factor for Nutritional Problems in the Elderly?," Physiology & behavior, 1999, vol. 66(2), pp. 199-201.
Bush M.L., et al., "Hot or cold? Is monothermal caloric testing useful and cost-effective?," The Annals ofOtology,Rhinology, and Laryngology,2013, vol. 122(6) pp. 412-416.
Cunha L.C., et al., "Validity of the monothermal caloric testing when compared to bithermal stimulation," Pro Fono., 2010, vol. 22(1), pp. 67-70.
Elkins R.L., "Conditioned Flavor Aversions to Familiar Tap Water in Rats: an Adjustment With Implications for Aversion Therapy Treatment of Alcoholism and Obesity," Journal of abnormal psychology, 1974, vol. 83(4), pp. 411-417.
"Geckskin", UMassAmherst, The College of Natural Sciences, retrieved from the Internet: https://geckskin.umass.edu/ on Jul. 3, 2017, 10 pages.
Health Technology Case Study 22, The Effectiveness and Costs of Alcoholism Treatment, Research on the Effectiveness of Alcoholism Treatment,Jul. 1973, pp. 43-53.
Knibb R.C., et al., "No Unique Role for Nausea Attributed to Eating a Food in the Recalled Acquisition of Sensory Aversion for That Food," Appetite, 2001, vol. 36(3), pp. 225-234.
Melagrana A., et al., "Comparison Between Air and Water Caloric Tests in Children," International Journal of Pediatric Otorhinolaryngology, Jul. 1999, vol. 51(3), 139-143.
Proctor L.R., "Clinical Experience With a Short-acting Caloric Test," Laryngoscope, Jan. 1985, vol. 95(1), pp. 75-80.
"Ultrathin Rechargeable Lithium Polymer Batteries from PowerStream," PowerStream, Jun. 29, 2017, retrieved from the Internet: https://www.powerstream.com/thin-lithium-ion.htm on Jul. 3, 2017, 4 pages.
Walther L.E., et al., "Caloric Stimulation With Near Infrared Radiation Does Not Induce Paradoxical Nystagmus," Acta otorhinolaryngologica Italica, 2011, vol. 31 (2), pp. 90-95.

* cited by examiner

| Name | Time to Trigger (m:s) | Hunger Level Before (1-10) | Hunger Level After (1-10) | Observations |
|---|---|---|---|---|
| MaryJo | 2:35 | 4 | 1 | Totally suppressed appetite for eating chocolate |
| Randy | 2:40 | 3 | 1 | I need to try again 15 mins before eating dinner |
| Conner H. 1st | 5 min | none | none | Balloon was in farther second time and he started feeling light headed in minute |
| Conner H. 2nd | 1:50 | 8 | 5 | Probably left in too little time. |
| Courtney | 2:00 | 3 | 0 | Got light headed and dizzy, she does have a light stomach |
| Colin | 4:10 | 3 | 1 | Jolly rancher tasted bitter afterwards, didn't want to keep it in. |
| Scott | 2:40 | 6 | 1 | 2 min after removal: more dizzy, slightly more nauseous |
| Davina | 2:00 | 4 | 1 | 2 min after removal: more nauseous, feeling comes on after, dizziness is immediate |
| Dan | 2:40 | 5 | 1 | a little dizzy and cannot walk a straight line |
| Anson | 7:00 | 7 | 2 | Feels a little off, a little dizzy |
| Scott | N/A | 6 | 4 | Went 5 min, little impact, ear felt cold, swerved when trying to walk straight, balloon not far enough in |
| Carly | N/A | 7 | N/A | Went 7 min, ear canal too small to fit balloon, but feels like she was on a boat |
| Annabelle | 1:42 | 5 | 1 | Ear was cold |
| Dan | 1:48 | 4 | 2 | A little dizzy and cannot walk a straight line |

FIG. 12

EAR APPARATUS AND METHODS OF USE

PRIORITY AND RELATED APPLICATIONS

This application claims priority to U.S. Provisional Patent Application Ser. No. 62/834,283 filed Apr. 15, 2019 entitled "EAR APPARATUS AND METHODS OF USE", which is incorporated herein by reference in its entirety.

The subject matter of this application is also generally related to that set forth in co-pending U.S. patent application Ser. No. 15/478,130 filed Apr. 3, 2017 and entitled "APPARATUS AND METHODS FOR EAR PROTECTION AND ENHANCEMENT" which claims priority to U.S. Provisional Patent Application Ser. No. 62/318,106 filed Apr. 4, 2016, of the same title, each of the foregoing being incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND

1. Technological Field

The disclosure relates to apparatus and methods for use of the ear and ear canal of a living being (such as a human) for behavioral control, and in one exemplary aspect to an ear apparatus and methods of use which enable selective control by a user (and/or other entity) of certain behaviors, including without limitation cravings for deleterious substances such as certain foods, alcohol, narcotics, or nicotine compulsions

2. Description of Related Technology

A number of different approaches to behavioral control of humans or animals are present in the prior art. One are of particular interest relates to behavior control in beings so as to mitigate or avoid deleterious effects on that being; e.g., over-consumption of food, smoking, alcohol intake, narcotics use, and the like. Generally, these existing approaches fall into one of several categories, including: (i) aversion therapy (where the being is conditioned to feel some negative sentiment or response) under certain scenarios, so as to condition them to exhibit less desire to engage in those scenarios; (ii) chemical means (e.g., pharmaceuticals which attempt to suppress the being's desire for the deleterious activity; or (iii) deprivation (i.e., reducing access to the deleterious activity or substance).

It is also known that at least in humans, caloric testing via the ear canal can produce various results in terms of how the test subject feels. A variety of literature is evidenced in the prior art relating to inter alia, caloric testing, including:

(i) Bush M L, Bingcang C M, Chang E T, Fornwalt B, Rayle C, Gal T J, Jones R O, Shinn J B., *Hot or cold? Is monothermal caloric testing useful and cost-effective?; Ann. Of Otology, Rhinology and Laryngoly.* 2013 June; 122(6): 412-6. PubMed PMID: 23837395;

(ii) Cunha L C, Felipe L, Carvalho S A, Labanca L, Tavares M C, Gonsalves D U., *Validity of the monothermal caloric testing when compared to bithermal stimulation; Pro Fono.* 2010 January-March; 22(1):67-70. English, Portuguese. PubMed PMID: 20339811;

(iii) Barros A C, Caovilla H H. *From nystagmus to the air and water caloric tests. Braz J Otorhinolaryngol.* 2012 July-August; 78(4):120-5. English, Portuguese. PubMed PMID: 22936148;

(iv) Melagrana A, D'Agostino R, Ravera B, Taborelli G., *Comparison between air and water caloric tests in children. Int J Pediatr Otorhinolaryngol.* 1999 Dec. 15; 51(3):139-43. PubMed PMID: 10628539;

(v) Proctor L R., *Clinical experience with a short-acting caloric test. Laryngoscope.* 1985 January; 95(1):75-80. PubMed PMID: 3965834;

(vi) Walther L E, Asenov D R, Di Martino E., *Caloric stimulation with near infrared radiation does not induce paradoxical nystagmus. Acta Otorhinolaryngol Ital.* 2011 April; 31(2):90-5. PubMed PMID: 22058588; PubMed Central PMCID: PMC3203743;

(vii) Knibb R C, Smith D M, Booth D A, Armstrong A M, Platts R G, Macdonald A, Booth I W., *No unique role for nausea attributed to eating a food in the recalled acquisition of sensory aversion for that food.* Appetite. 2001 June; 36(3):225-34. PubMed PMID: 11358346;

(viii) Bernstein I L., *Food aversion learning: a risk factor for nutritional problems in the elderly?*, Physiol Behav. 1999 April; 66(2):199-201. Review. PubMed PMID: 10336144; and (ix) Elkins R L., *Conditioned flavor aversions to familiar tap water in rats: an adjustment with implications for aversion therapy treatment of alcoholism and obesity. J Abnorm Psychol.* 1974 August; 83(4):411-7. PubMed PMID: 4412581.

See also *Behavior Therapy in Psychiatry*, Task Force Report 5, American Psychiatric Association (July 1973), as well as *Research on the Effectiveness of Alcoholism Treatment*, (Health Technology Case Study 22: The Effectiveness and Costs of Alcoholism Treatment; https://www.princeton.edu/~ota/disk3/1983/8307/830707 PDF) regarding stimuli that can be used for aversion.

None of the foregoing, however, enable effective treatment or control of behaviors (including the deleterious behaviors described above) in a simple to use, non-prescription, and user-controllable form; each require at least one of (i) intervention of a specialist or health care provider, (ii) ingestion or use of medications or pharmaceuticals (which may have their own deleterious effects), (iii) high cost; and/or (iv) lack of efficacy.

Hence, based on the foregoing, what is needed is safe and effective apparatus and methods which can be used for behavior influence or control in living beings.

SUMMARY

The present disclosure addresses the foregoing needs by providing, inter alia, an improved apparatus and methods for behavior control of living beings such as humans.

In one aspect, an apparatus that induces the caloric effect to modify a human behavior is disclosed. In one embodiment, the apparatus includes a mechanism for reducing or increasing the local temperature within at least a portion of an ear canal of a human being. In various implementations, this mechanism can include for example: (i) a gaseous medium, (ii) a liquid medium, (iii) radiative energy such as IR or frequencies of electromagnetic radiation, and/or (iv) a thermally conductive solid medium.

In one implementation, a compliant balloon-like structure is used as a heat transfer medium (whether into or from the tissue in the ear canal), so as to enable a high degree of surface area/contact between the thermal working medium (inside the balloon) and the tissue via the compliant material of the balloon. In one approach, an elastomer is used such that when the balloon is filled ("inflated") with the working medium, it has a high degree of conformance to the tissue surrounding it.

In another aspect of the disclosure, a selectively operable or actuated ear temperature control apparatus is described. In one embodiment, the apparatus includes an ear insert or plug having a valve assembly therein which permits modulation of an amount of air and/or water or other fluidic medium that enters the ear canal from an exterior environment so as to control caloric effect.

In one variant, the valve assembly is accessible to and manually operable by the wearer with e.g., a tip of one finger. In one implementation, the valve assembly comprises a substantially planar element disposed at least partly on an exterior surface of the body of the ear plug, and is configured such that a wearer of the apparatus can actuate the valve via rotation of the substantially planar element around an axis, the axis disposed substantially perpendicular to a plane of the planar element.

In another variant, the valve assembly is selectively (and passively) actuated or de-actuated via a thermally reactive material within at least a portion of the plug body.

In another variant, the plug is designed to cooperate with one or more anatomical features of the wearer such that it is retained within the ear canal with a minimum depth of insertion, and maximum degree of comfort. In one implementation, the one or more anatomical features include the tragus of the outer ear of a human being. In another implementation, the so-called "conchal Incisura" is utilized to assist in, inter alia, maintaining the desired orientation (including roll prevention), position, and lead-in for alignment during insertion.

In a further variant, the exterior material(s) of at least a portion of the outer plug body is configured to aid in retention of the ear plug within the outer ear canal. In one variant, the material comprises a plurality of synthetic "micro-setae" disposed on the outer surface of the plug body so as to enable the setae to interact with the surface of the dermis of the wearer's ear canal tissue, thereby largely obviating generally undesirable outward bias pressures which can lead to irritation of such sensitive tissues.

In a further variant, a chemical ampule is disclosed which, based on its chemical reaction, can be endothermic or exothermic and used for application of thermal stimulus.

In another variant, a reusable "ice cube" or other form factor is disclosed. In one implementation, a sealed polymer enclosure with water or other suitable fluid contained therein is configured to allow freezing (such as via the user's kitchen freezer), and is shaped so as to properly position itself proximate to the applicable ear canal surfaces when inserted by the user such that thermal stimuli can be applied.

In yet a further variant, the plug is configured to be retained in place via an external mechanism (whether alone or in conjunction with the foregoing cooperation with the anatomical features of the wearer). In one implementation, the mechanism comprises a magnetic backing plate which interacts with a magnet of the ear plug through the tissue of the wearer.

In another implementation, the plug is configured to be retained at least partly via an internal mechanism of the plug; e.g., a circumferentially expanding ring or region which contacts a portion of the inner surface of the outer portion of the ear canal, and which can be selectively actuated by the wearer.

In a further implementation, the plug is configured to be retained at least partly via an internal mechanism of the plug; e.g., a circumferentially expanding ring or region which contacts a portion of the inner surface of the outer portion of the ear canal under interior spring assembly expansive force.

In yet a further implementation, the plug is sized and shaped so as to be retained generally in the desired place, but not provide a complete seal around its periphery with the surrounding ear tissue, seeking only to mitigate fluid or air flow into or out of the ear canal, and not completely prevent it, thereby maximizing comfort for the wearer during periods of extended use.

In a further aspect, a method of treating a patient with behavioral condition or deficiency is disclosed. In one embodiment, the method includes installing a selectively variable or controllable apparatus within the ear canal; adjusting at least one aspect of the apparatus so as to permit a desired amount of air and/or other medium into the canal during normal wear; and monitoring the effect on the patient being treated to determine or identify a desired effect thereon.

In a further aspect, a method of using an ear apparatus to selectively impose a caloric effect on a living being is disclosed.

In yet a further aspect, methods of installing and removing an ear apparatus are disclosed.

In another aspect, apparatus for mechanical retention of a caloric control ear apparatus are disclosed. In one embodiment, the apparatus for retention comprises a substantially planar and curved structure with a magnetic element associated therewith; the magnetic element generates a magnetic field that at least partly permeates through the wearer's outer ear tissue to interact with a corresponding ferrous or other magnetized element within an ear apparatus oriented so as to cause attraction between the two elements through the user's tissue, thereby retaining the ear apparatus (and the planar curved structure) in a substantially constant orientation and position.

In another aspect, electronic apparatus is disclosed. In one embodiment, the electronic apparatus includes an outer body, and an interior cavity configured to contain a plurality of electronic components. In one variant, the components include a temperature sensor (e.g., thermocouple or RTD), Bluetooth transceiver, and a micro-fan assembly. The micro-fan assembly in one implementation comprises a small rotary fan structure to generate air movement into/out of the ear canal through one or more channels formed within the outer body. A micro (e.g., flat planar and flexible) lithium ion battery is included in the cavity to power the electronic components and fan. The battery can be recharged inductively, thereby obviating exposed electrical terminals.

In another variant, the components include a Wi-Fi transceiver (e.g., Wi-Fi or Wi-Fi "Direct" enabled) that modulates its transmission power within the frequency band of interest to communicate only with very nearby Wi-Fi enabled devices (e.g., the user's smartphone or tablet when in their immediate possession or jacket pocket), so as to mitigate electromagnetic radiation (EMR) dose to the wearer when in use.

In a further variant, an IEEE Std. 802.15 PAN enabled integrated circuit device (e.g., Zigbee® or the like) or BLE (Bluetooth Low Energy) device is utilized within the apparatus.

In another variant, the electronic apparatus is configured as a selectively actuated ear device, and the plug(s) act as one or more "IoT" ("Internet of things") entities such that it can receive and/or transmit data of utility in various types of applications.

In another aspect, a method of characterizing a user in terms of caloric effect response is disclosed. In one embodiment, the method includes inserting a selectively controllable caloric apparatus into the user's ear canal, and invoking various stimuli (increase and decrease in temperature for varying periods of time), and observing or recording the user's reaction(s) to the various stimuli. From this data, an optimized user-specific profile may be generated, which may also vary from one ear to the other on a given user (e.g., ear-specific profiles may be generated and utilized by the apparatus during subsequent operation).

Other features and advantages of the present disclosure will immediately be recognized by persons of ordinary skill in the art with reference to the attached drawings and detailed description of exemplary embodiments as given below.

BRIEF DESCRIPTION OF THE DRAWINGS

FIG. 12 is a tabular representation showing exemplary test results obtained by the inventors hereof using a prototype ear apparatus for caloric effect control of appetite suppression.

Figure 1:
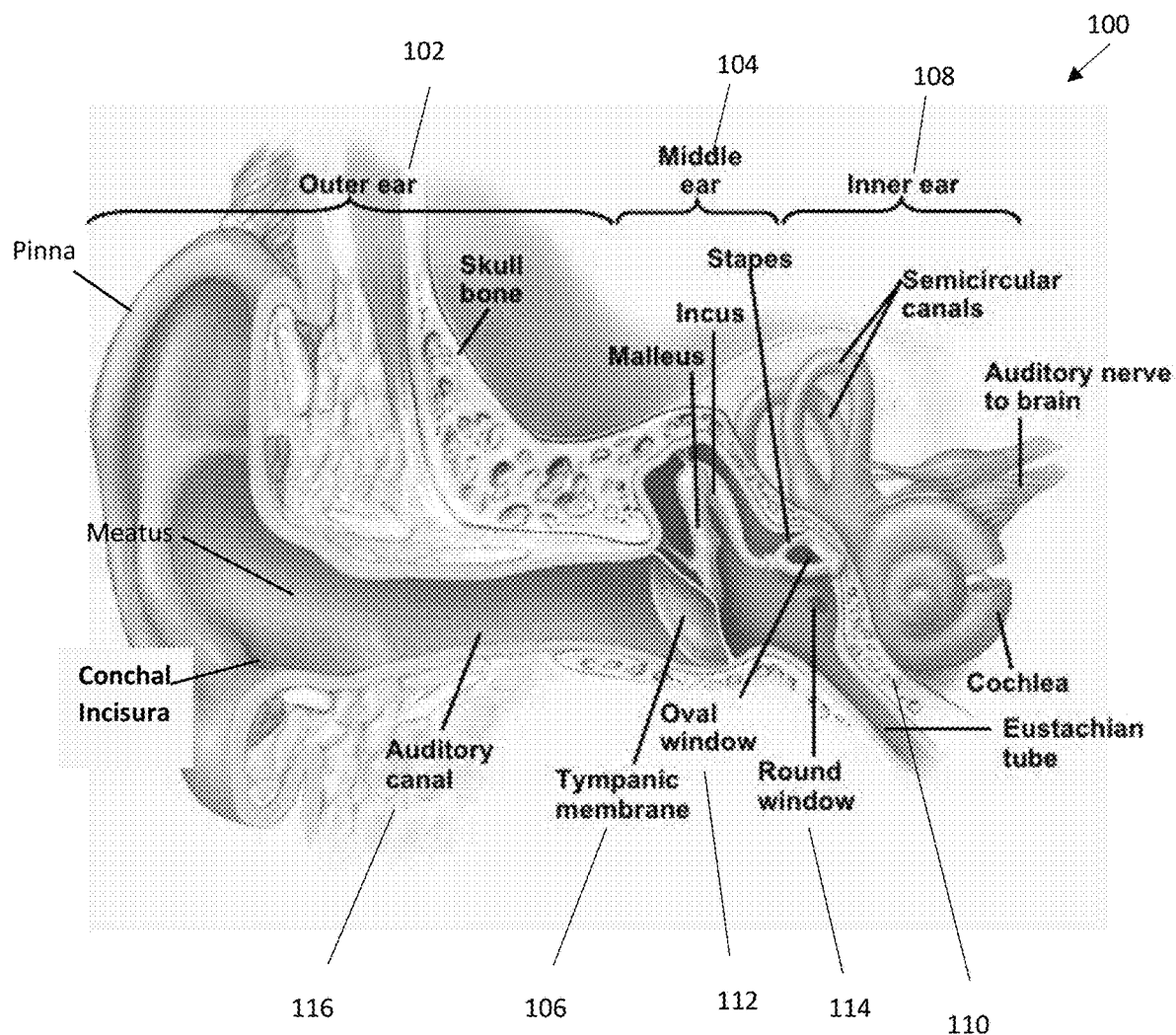
FIG. 1 is a cross-sectional view of a typical human ear, illustrating various anatomical features thereof.

All figures © Copyright 2019-2020 MD Idea Factory. All rights reserved.

DESCRIPTION OF THE DISCLOSURE

Reference is now made to the drawings wherein like numerals refer to like parts throughout.

As used herein, the term "access point" refers generally and without limitation to a network node which enables communication between a user or client device and another entity within a network, such as for example a Wi-Fi AP, or a Wi-Fi-Direct enabled device acting as a Group Owner (GO).

As used herein, the term "application" refers generally and without limitation to a unit of executable software that implements a certain functionality or theme. The themes of applications vary broadly across any number of disciplines and functions (such as on-demand content management, e-commerce transactions, brokerage transactions, home entertainment, calculator etc.), and one application may have more than one theme. The unit of executable software generally runs in a predetermined environment; for example, the unit could include a downloadable Java Xlet™ that runs within the JavaTV™ environment.

As used herein, the term "client device" includes, but is not limited to, set-top boxes (e.g., DSTBs), gateways, modems, personal computers (PCs), and minicomputers, whether desktop, laptop, or otherwise, and mobile devices such as handheld computers, PDAs, personal media devices (PMDs), tablets, "phablets", smartphones, and vehicle infotainment or similar systems. As used herein, the term "codec" refers to a video, audio, or other data coding and/or decoding algorithm, process or apparatus including, without limitation, those of the MPEG (e.g., MPEG-1, MPEG-2, MPEG-4/H.264, etc.), Real (RealVideo, etc.), AC-3 (audio), DiVX, XViD/ViDX, Windows Media Video (e.g., WMV 7, 8, 9, 10, or 11), ATI Video codec, or VC-1 (SMPTE standard 421M) families.

As used herein, the term "computer program" or "software" is meant to include any sequence or human or machine cognizable steps which perform a function. Such program may be rendered in virtually any programming language or environment including, for example, C/C++, Fortran, COBOL, PASCAL, assembly language, markup languages (e.g., HTML, SGML, XML, VoXML), and the like, as well as object-oriented environments such as Java™ (including J2ME, Java Beans, etc.) and the like.

As used herein, the terms "Internet" and "internet" are used interchangeably to refer to inter-networks including, without limitation, the Internet. Other common examples include but are not limited to: a network of external servers, "cloud" entities (such as memory or storage not local to a device, storage generally accessible at any time via a network connection, and the like), service nodes, access points, controller devices, client devices, etc.

As used herein, the term "memory" includes any type of integrated circuit or other storage device adapted for storing digital data including, without limitation, ROM, PROM, EEPROM, DRAM, SDRAM, DDR/2 SDRAM, EDO/FPMS, RLDRAM, SRAM, "flash" memory (e.g., NAND/NOR), and PSRAM.

As used herein, the terms "microprocessor" and "processor" or "digital processor" are meant generally to include all types of digital processing devices including, without limitation, digital signal processors (DSPs), reduced instruction set computers (RISC), general-purpose (CISC) processors, microprocessors, gate arrays (e.g., FPGAs), PLDs, reconfigurable computer fabrics (RCFs), array processors, secure microprocessors, and application-specific integrated circuits (ASICs). Such digital processors may be contained on a single unitary IC die, and/or distributed across multiple components.

As used herein, the term "network" refers generally to any type of telecommunications or data network including, without limitation, data networks (including MANs, WANs, LANs, WLANs, internets, and intranets). Such networks or portions thereof may utilize any one or more different topologies (e.g., ring, bus, star, loop, etc.), transmission media (e.g., wired/RF cable, RF wireless, millimeter wave, optical, etc.) and/or communications or networking protocols (e.g., SONET, DOCSIS, IEEE Std. 802.3, ATM, X.25, Frame Relay, 3GPP, 3GPP2, LTE, WAP, SIP, UDP, FTP, RTP/RTCP, H.323, etc.).

As used herein, the term "network interface" refers to any signal or data interface with a component or network including, without limitation, those of the IEEE-1394, USB (e.g., USB2), Ethernet (e.g., 10/100, 10/100/1000 (Gigabit Ethernet), 10-Gig-E, etc.), Wi-Fi (802.11), WiMAX (802.16), Zigbee®, Z-wave, PAN (e.g., 802.15, Bluetooth, BLE), power line carrier (PLC), or IrDA families.

As used herein, the term "shape memory alloy" or "SMA" shall be understood to include, but not be limited to, any metal that is capable of "remembering" or substantially reassuming a previous geometry. For example, after it is deformed, it can either substantially regain its original geometry by itself during e.g., heating (i.e., the "one-way effect") or, at higher ambient temperatures, simply during unloading (so-called "pseudo-elasticity"). Some examples of shape memory alloys include nickel-titanium ("NiTi" or "Nitinol") alloys and copper-zinc-aluminum alloys.

As used herein, the term "Wi-Fi" refers to, without limitation and as applicable, any of the variants of IEEE-Std. 802.11 or related standards including 802.11 a/b/g/n/s/v/ac or 802.11-2012/2013, 802.11-2016, as well as Wi-Fi Direct (including inter alia, the "Wi-Fi Peer-to-Peer (P2P) Specification", incorporated herein by reference in its entirety).

As used herein, the term "wireless" means any wireless signal, data, communication, or other interface including without limitation Wi-Fi, Bluetooth, BLE (Bluetooth Low Energy), 3G/4G/4.5G/5G (3GPP/3GPP2), HSDPA/HSUPA, TDMA, CDMA (e.g., IS-95A, WCDMA, etc.), FHSS, DSSS, GSM, PAN/802.15, WiMAX (802.16), 802.20, Zigbee®, Z-wave, narrowband/FDMA, OFDM, PCS/DCS, LTE/LTE-A, NR (New Radio), analog cellular, CDPD, satellite systems, millimeter wave or microwave systems, acoustic, and infrared (i.e., IrDA).

Overview

In one aspect, improved apparatus for control of physiological responses and/or behavior of a living being, and related methods of use and operation are disclosed herein. In one embodiment, the apparatus (which in some variants may be selectively controllable by the user or a software process such as an app, or even third-party entity or process) is configured to be insertable and removable within an ear canal of a user. The apparatus in one implementation makes use of the caloric effect to induce certain physiologic responses in the being (e.g., human) so as to control or influence certain behaviors such as cravings for smoking, narcotics, alcohol, food, or other potentially deleterious substances. It is also contemplated that the apparatus may be selectively controlled to stimulate certain responses or behaviors which may be desired via caloric effects.

In one example, the apparatus is inserted into a user's ear canal. After insertion, the apparatus is selectively controlled by the user, or a health care professional, or by a supervisory process (e.g., computer program) operative to run on the apparatus or a connected device such as a smartphone, laptop, desktop, etc. The control determines how much caloric stimulation is added/removed to the user, such as according to a desired profile.

The exemplary embodiment of the apparatus may also be optionally designed to avoid too deep insertion into the ear canal (where overly deep insertion may cause potential structural damage to the ear)

Variants of the disclosed apparatus include miniature devices insertable within the ear that include onboard digital memory, processing, and wireless interfaces for e.g., control and data transmission/reception via an application operative on a user's smartphone.

Anatomy and Caloric Effect

A brief discussion of the exemplary human ear anatomy is useful in further explanation of the various features and advantages of the apparatus and methods of the present disclosure.

Referring now to FIG. 1, a cross section of a typical human ear 100 (viewed from a front perspective) is shown. In general, the ear includes an outer (external) ear 102, a middle ear 104 separated from the outer ear by a tympanic membrane (TM) 106, and an inner ear 108 separated from the middle ear by a wall of boney tissue 110 including two small 2.5 mm$^2$ "windows"—an oval window footplate at the base of the stapes 112 and a soft tissue round window membrane (RWM) 114.

As is known, the caloric effect uses a fluidic medium (water or air) to induce a desired effect to test for e.g., physiologic response of the vestibular nerves. For instance, so-called "caloric stimulation" or caloric reflex testing is a test that uses differences in temperature to diagnose or confirm a diagnosis of damage to the vestibular nerve, and/or damage to the brain stem. The test stimulates the vestibular nerve by delivering cold or warm water or air into the test subject's ear canal. When cold water or air enters the ear and the inner ear changes temperature, it induces (at least in a normal subject) fast, side-to-side eye movements called nystagmus.

However, the inventors of the present disclosure have observed that selective exposure of portions of the ear canal or the inner ear to certain temperatures for certain times can result in behavioral changes from the standpoint of desire for certain substances such as food, alcohol, or narcotics. Specifically, depending on the profile (e.g., time/temperature) used, removal of feelings of hunger or desire for alcohol or narcotics can be achieved via creation of a mild nausea or pre-nausea state (or in some cases even more severe), which suppresses these urges. The effect is temporary, completely reversible, yet effective as demonstrated by e.g., the test data set forth herein.

Description of Exemplary Embodiments

It is noted that while the apparatus of the disclosure described herein are discussed primarily with respect to use in a personal context, such as by consumer, certain aspects of the disclosure may be useful in other applications, including, without limitation, non-recreational consumer use (e.g., in a medical office or health care facility), in industrial applications (e.g., to selectively control user desire for "smoke breaks" or the like); in military, government or other applications (e.g., in aircraft, spacecraft, submersibles or submarines); in communications or entertainment applications/systems (e.g., personal media devices, consumer electronics, or automotive applications); and in therapy applications.

It is also noted that while the ear apparatus of the disclosure is described herein primarily in the context of a human wearer or user, many of the principles and features of the disclosure are adaptable to other species and their particular anatomical features including, without limitation, primates such as e.g., chimpanzees.

Yet further, while certain aspects and methods are described with respect to use on a single ear of the wearer, it will be recognized that the methods and apparatus may be used with more than one ear, whether contemporaneously or at different times, including without limitation: (i) selective switching from ear to ear, (iii) use in concert in differential fashion (i.e., differently with respect to one ear as compared to the other).

One side effect of the caloric stimulation described herein with respect to the exemplary embodiments is rapid eye movement (REM). Such REM generally starts at a slow frequency, and accelerates as the duration of the stimulation is lengthened. Moreover, the longer that the stimulation is applied, the more/more intense the resulting nausea that the subject feels. In anecdotal testing provided by the inventors hereof, after about 4-5 minutes (utilizing ice water as a stimulation medium), the subject has been observed to feel as if they have a terrible sea-sickness. This longer duration accordingly may be used to alter more addictive behaviors.

In exemplary implementations, at the point when the subject's eye(s) begin to perceptibly twitch (e.g., a rotation of the subject's eyeball on the order of a few degrees such that it can be visually perceived, including in some cases where the eyelid is closed and the underlying "twitch" can be seen via movement of the eyelid itself) is correlated to a feeling of mild "queasiness" in the subject, without any significant nausea. See discussion of FIG. 10. This point of the therapy is significant for, inter alia, hunger satiation/suppression, since it is a readily ascertainable event, and is also a boundary for further (more severe) aversion stimulus equating to a greater feeling of nausea. As such, exemplary embodiments of the apparatus and methods described herein make use of this observation in determining the duration of stimulus to apply.

Exemplary Apparatus—

Various embodiments of the caloric effect apparatus according to the present disclosure are now described. As described in greater detail below, the apparatus in its various incarnations includes a mechanism for increasing and/or reducing the local temperature within at least a portion of an ear canal of a human being. In various implementations, this mechanism can include: (i) a gaseous medium (such as compressed gas being released and which naturally cools as it reaches ambient pressure, such as e.g., a $CO_2$ cylinder), (ii) a liquid medium (including pseudo-liquids such as gels), (iii) radiative energy such as IR or other wavelengths of electromagnetic radiation, and/or (iv) a thermally conductive solid medium.

In another aspect of the disclosure, a selectively operable or actuated ear temperature control apparatus is described. In one embodiment, the apparatus includes an ear insert or plug having a valve assembly therein which permits modulation of an amount of air and/or water or other fluidic medium that enters the ear canal (or any container member such as a balloon for liquids) from an exterior environment so as to control caloric effect. To this end, the user may increase/decrease the temperature increase/decrease and rate as needed manually, so as to adjust the device for optimal effect. As described below, in some embodiments, these parameters may be controlled via PID or feedback loop or other control logic as well or in the alternative.

In one variant, the valve assembly is accessible to and manually operable by the wearer with e.g., a tip of one finger. In one implementation, the valve assembly comprises a substantially planar element disposed at least partly on an exterior surface of the body of the ear plug, and is configured such that a wearer of the apparatus can actuate the valve via rotation of the substantially planar element around an axis, the axis disposed substantially perpendicular to a plane of the planar element.

In another variant, the operation of the caloric effect apparatus is selectively (and passively) actuated or de-actuated via a thermally reactive material within at least a portion of the plug body. For instance, as the temperature of the apparatus adjusts (to that within the ear canal after insertion), the effect imparted by the apparatus (whether heating or cooling) can change as a result.

In another variant, the apparatus is configured as an ear plug; e.g., one that is designed to cooperate with one or more anatomical features of the wearer such that it is retained within the ear canal with a minimum depth of insertion, and maximum degree of comfort. See, e.g., the exemplary methods and apparatus described in co-pending U.S. patent application Ser. No. 15/478,130 filed Apr. 3, 2017 and entitled "APPARATUS AND METHODS FOR EAR PROTECTION AND ENHANCEMENT" which claims priority to U.S. Provisional Patent Application Ser. No. 62/318,106 filed Apr. 4, 2016, of the same title, each of the foregoing being incorporated herein by reference in its entirety. In one implementation, the one or more anatomical features include the tragus of the outer ear of a human being. In another implementation, the so-called "conchal Incisura" is utilized to assist in, inter alia, maintaining the desired orientation (including roll prevention), position, and lead-in for alignment during insertion.

In a further variant, the exterior material(s) of at least a portion of the outer plug body is configured to aid in retention of the ear plug within the outer ear canal. In one variant, the material comprises a plurality of synthetic "micro-setae" disposed on the outer surface of the plug body so as to enable the setae to interact with the surface of the dermis of the wearer's ear canal tissue, thereby largely obviating generally undesirable outward bias pressures which can lead to irritation of such sensitive tissues.

In yet a further variant, the plug is configured to be retained in place via an external mechanism (whether alone or in conjunction with the foregoing cooperation with the anatomical features of the wearer). In one implementation, the mechanism comprises a magnetic backing plate which interacts with a magnet of the ear plug through the tissue of the wearer.

In another implementation, the plug is configured to be retained at least partly via an internal mechanism of the plug; e.g., a circumferentially expanding ring or region which contacts a portion of the inner surface of the outer portion of the ear canal, and which can be selectively actuated by the wearer.

In a further implementation, the plug is configured to be retained at least partly via an internal mechanism of the plug; e.g., a circumferentially expanding ring or region which contacts a portion of the inner surface of the outer portion of the ear canal under interior spring assembly expansive force.

In yet a further implementation, the "plug" or insert apparatus is sized and shaped so as to be retained generally in the desired place, but not provide a complete seal around its periphery with the surrounding ear tissue, seeking only to mitigate fluid or air flow into or out of the ear canal, and not completely prevent it, thereby maximizing comfort for the wearer during periods of extended use.

In a further variant, a chemical ampule is disclosed which, based on its chemical reaction, can be endothermic or exothermic and used for application of thermal stimulus.

In another variant, a reusable "ice cube" or other form factor is disclosed. In one implementation, a sealed polymer enclosure with water or other suitable fluid contained therein is configured to allow freezing (such as via the user's kitchen freezer), and is shaped so as to properly position itself proximate to the applicable ear canal surfaces when inserted by the user such that thermal stimuli can be applied. In one variant, the enclosure may be itself thermally formed (such as via immersion in boiling water prior to use) to soften it suitably so that it can be inserted into the particular user's ear canal and as it cools, assume the shape of that user's canal. In another variant, a 3D-printed model is used, the model based on imagery and or other measurement date accurately describing the configuration of the particular user's ear canal.

Figure 2:
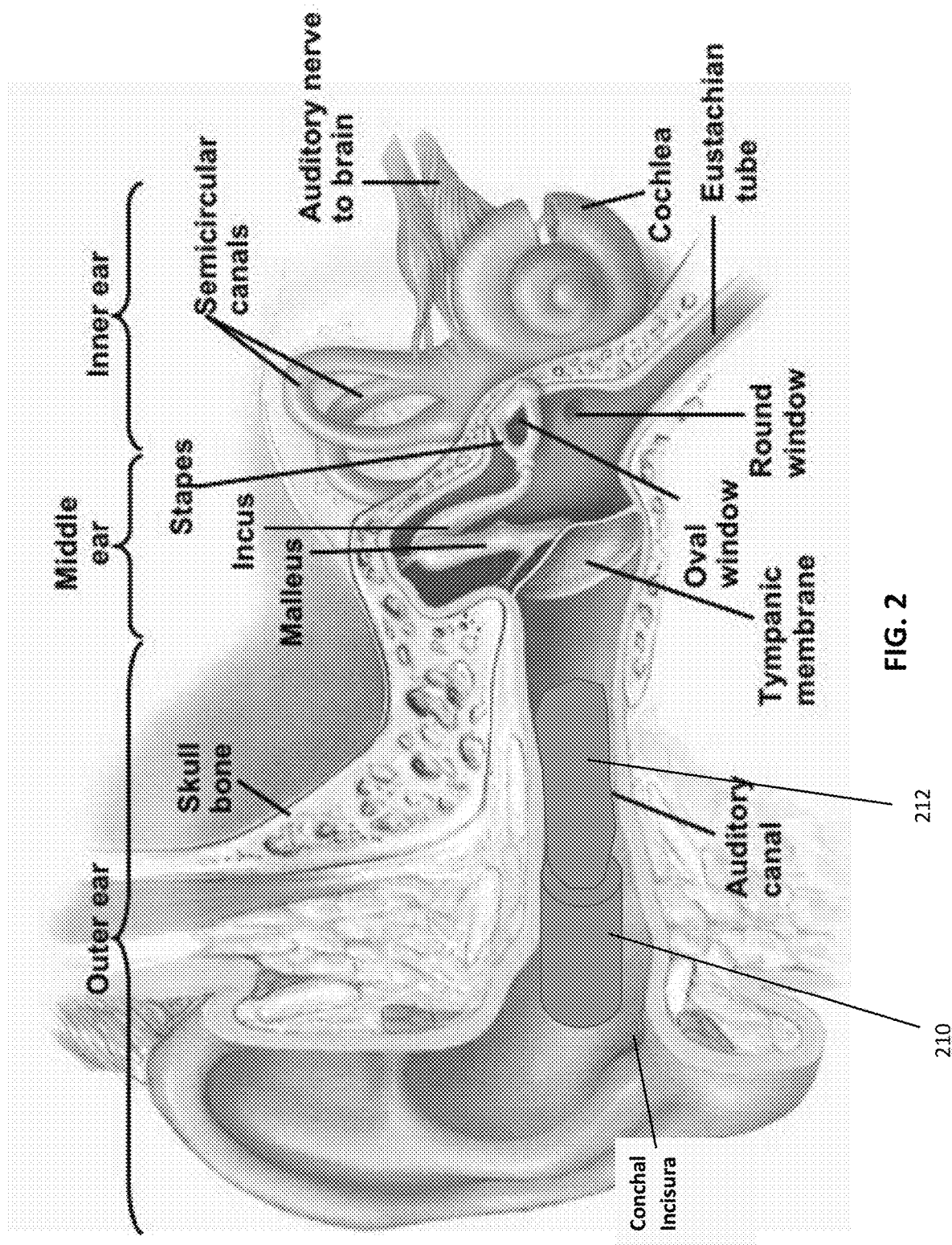
FIG. 2 is a cross-sectional view of an ear canal with one embodiment of the ear apparatus of the present disclosure using a balloon element.

FIG. 2 is a cross-sectional view of an ear canal with one embodiment of the ear apparatus of the present disclosure using a balloon element. In this embodiment, a compliant balloon-like structure is used as a heat transfer medium (whether into or from the tissue in the ear canal), so as to enable a high degree of surface area/contact between the thermal working medium (inside the balloon) and the tissue via the compliant material of the balloon. In one approach, an elastomer is used such that when the balloon is filled ("inflated") with the working medium, it has a high degree of conformance to the tissue surrounding it. The working medium may be gaseous or liquid. For instance in one variant, $CO_2$ (carbon dioxide) in a compressed form is released into the inner chamber of the balloon 212 via the body element 210 (e.g., from a miniature $CO_2$ cylinder and valve) so as to inflate the balloon and cause the desired level of contact and hence cooling—as the $CO_2$ expands upon release from the pressurized cylinder, it cools appreciably, and this draws heat from the ear canal surface through the balloon material. Likewise, using chilled water (relative to ear canal temperature), the balloon in another variant is "inflated" with chilled water to achieve a similar effect. Note that the latent heats of the liquid and gaseous media may be significantly different, and hence the present disclosure contemplates control and PID or feedback loops to control the rate of introduction of the medium (and hence temperature change and rate of temperature change within the ear canal) as can be appreciated by those of ordinary skill in the art.

Figure 3:
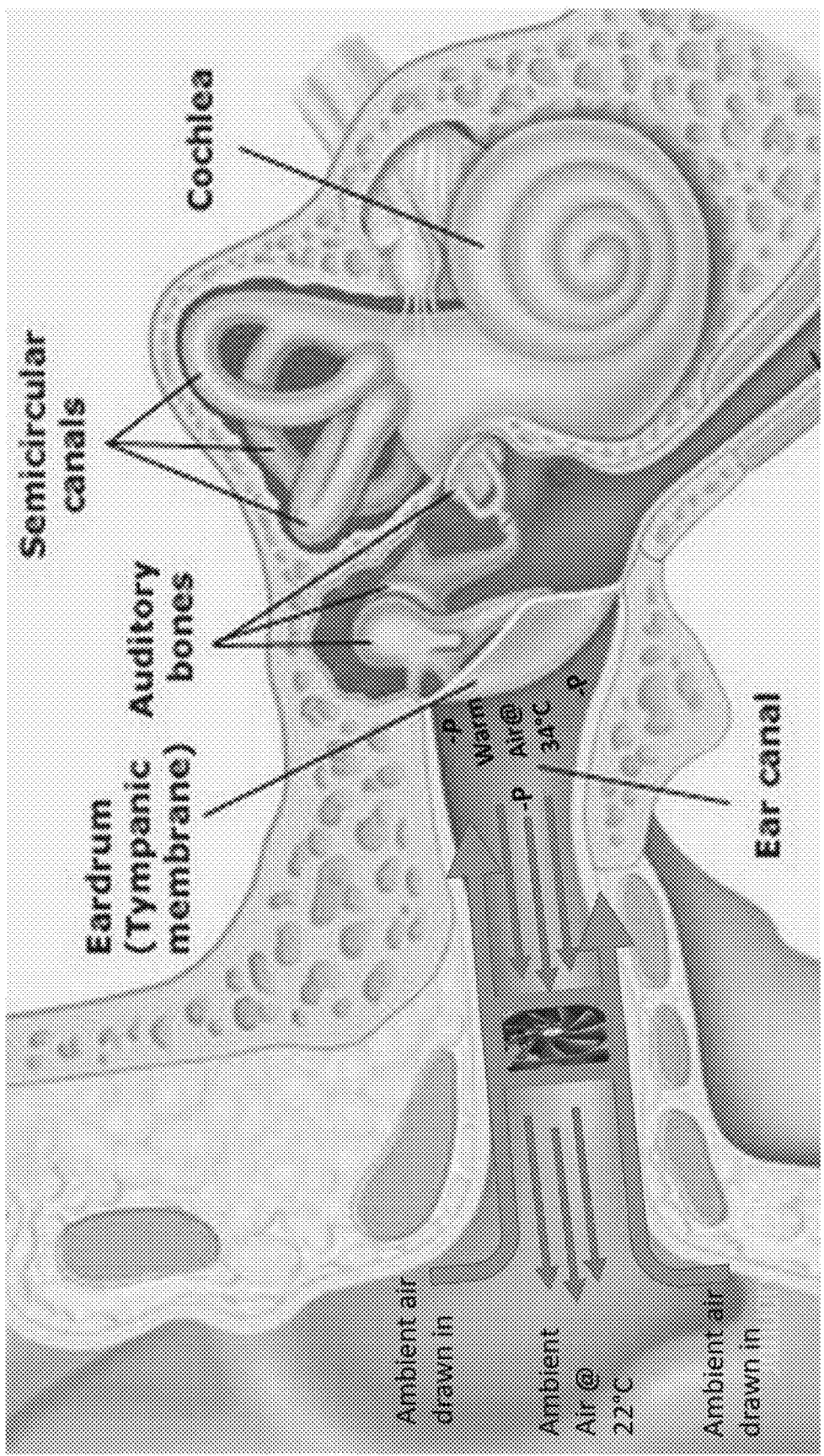
FIG. 3 is a cross-sectional view of an ear canal with one embodiment of the ear apparatus of the present disclosure used for cooling.

FIG. 3 is a cross-sectional view of an ear canal with one embodiment of the ear apparatus of the present disclosure used for cooling. In this embodiment, a negative pressure is created in the ear canal by removing warm air and forcing cool air to replace it by entering the canal. Specifically, in one variant, the air within the canal is exhausted by the fan or other motive force, thereby causing a pressure differential across the interior of the canal and the exterior of the ear, and drawing ambient (cooler) air inward as shown.

Figure 4A:
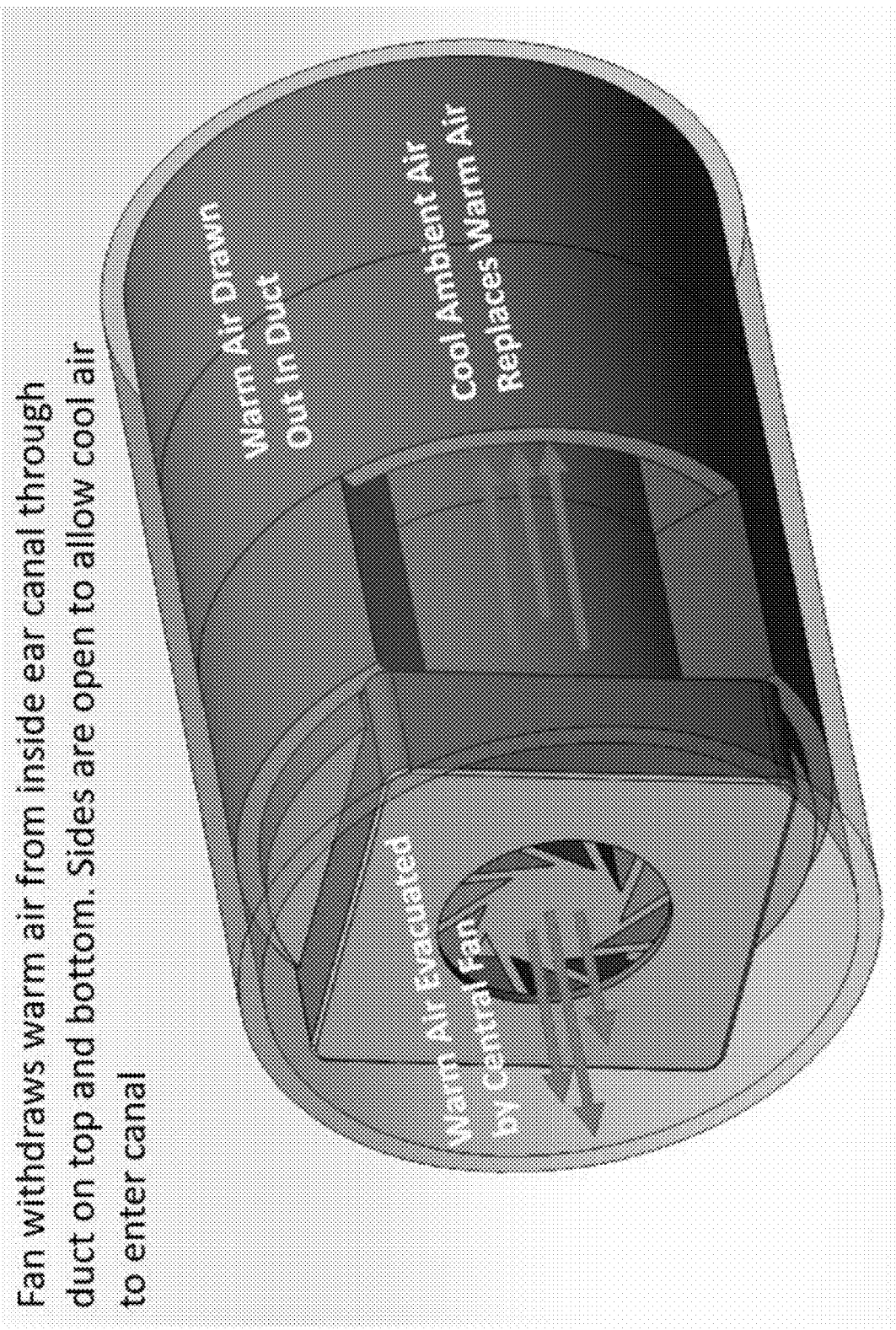
FIG. 4a is a perspective view of one embodiment of the ear apparatus of the disclosure showing air movement relative thereto.

FIG. 4a is a perspective view of one embodiment of the ear apparatus of FIG. 3 showing air movement relative thereto.

Figure 4B:
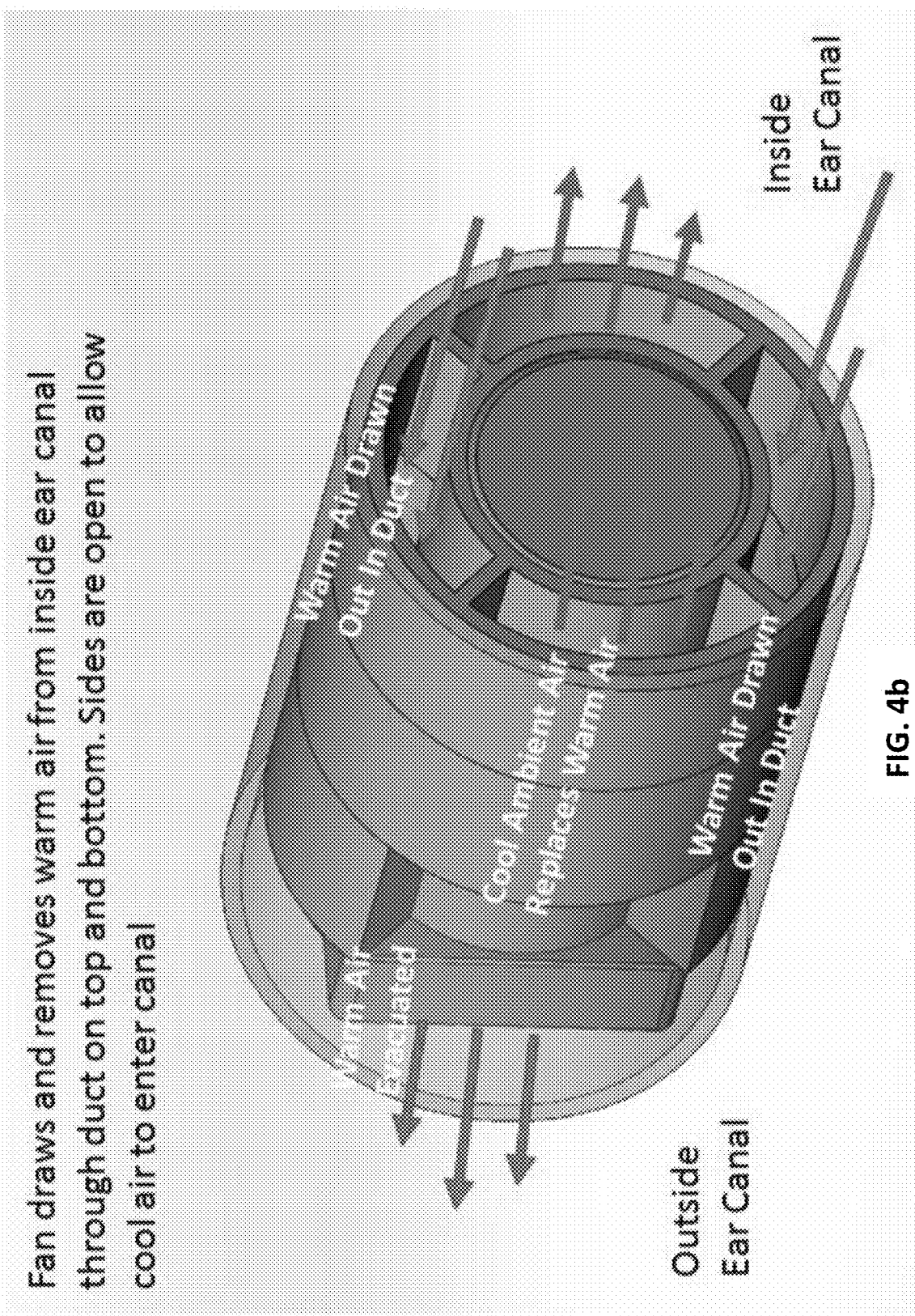
FIG. 4b is a perspective view of another embodiment of the ear apparatus of the disclosure showing air movement relative thereto.

FIG. 4b is a perspective view of another embodiment of the ear apparatus of FIG. 3 showing air movement relative thereto.

In some exemplary configurations, a peripheral passive ingress channel which allows cool air to enter the inner ear space due to negative pressure created by central egress fan port is utilized (i.e., the fan or other air exhaust mechanism creates a comparatively lower pressure inside the enclosed space, which according draws higher pressure (cool) air in around the periphery of the fan or exhaust mechanism.

Figure 5:
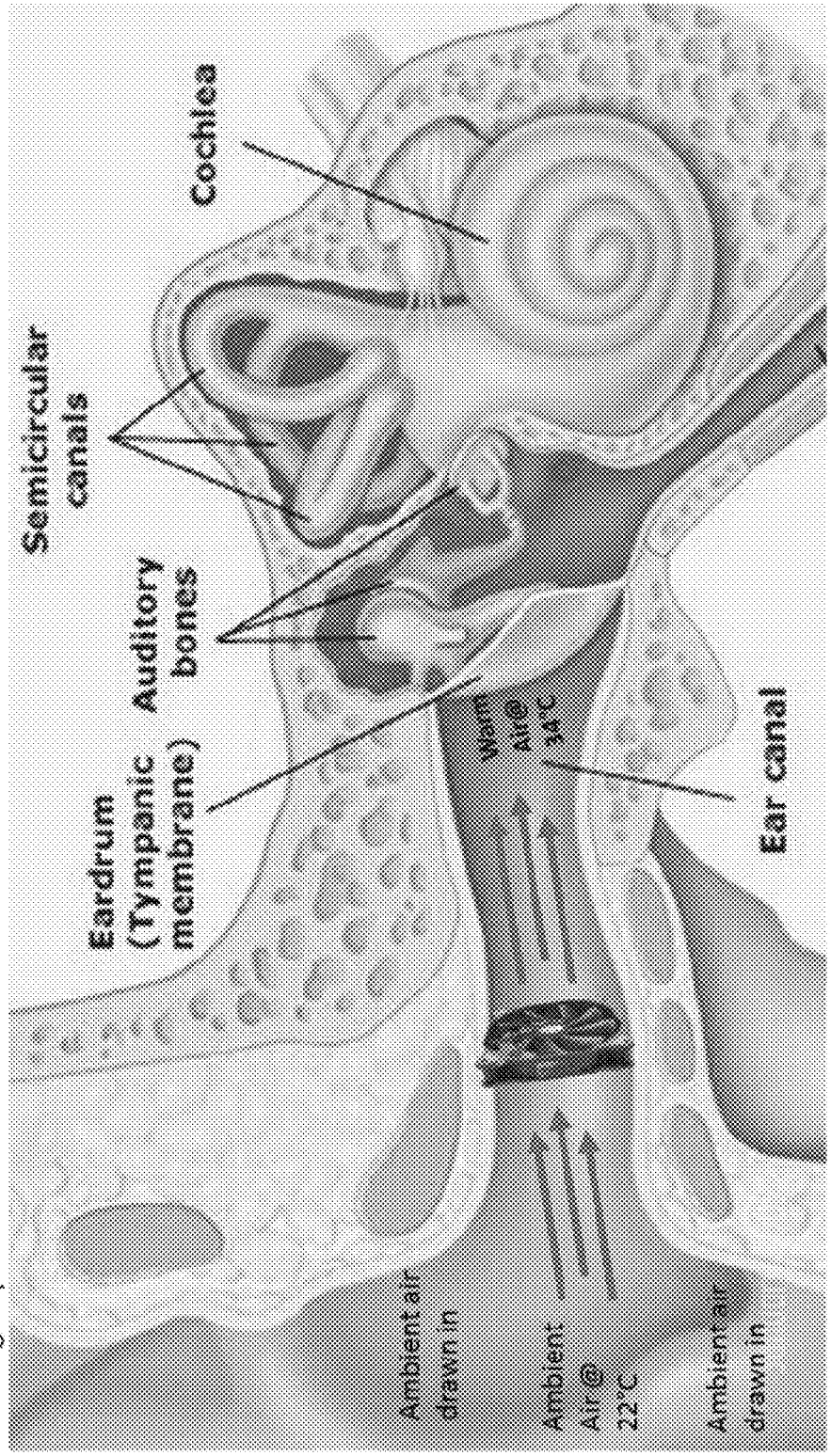
FIG. 5 is a cross-sectional view of an ear canal with another embodiment of the ear apparatus of the present disclosure used for cooling.

FIG. 5 is a cross-sectional view of an ear canal with another embodiment of the ear apparatus of the present disclosure used for cooling.

Figure 6:
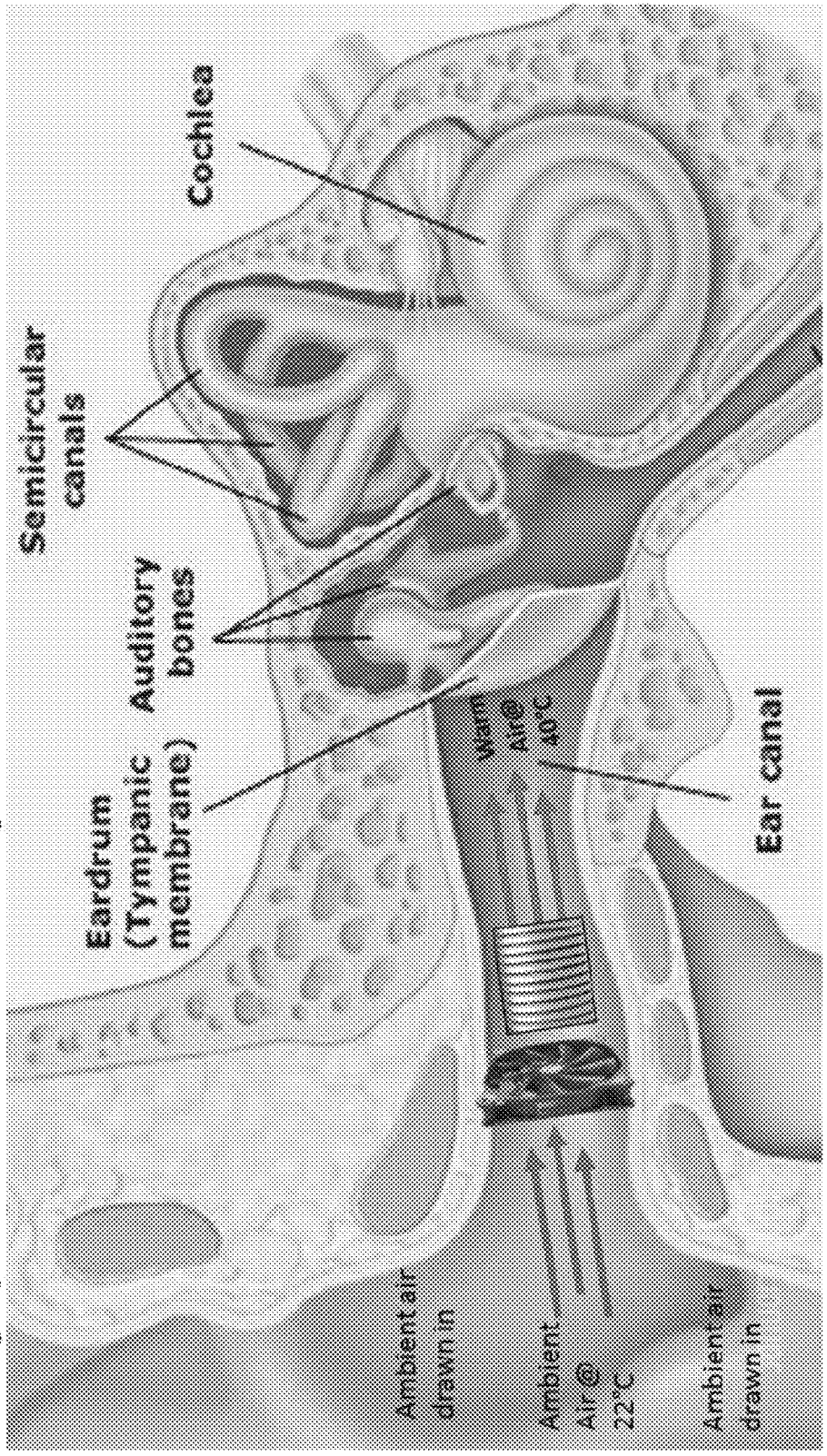
FIG. 6 is a cross-sectional view of an ear canal with one embodiment of the ear apparatus of the present disclosure used for heating.

FIG. 6 is a cross-sectional view of an ear canal with one embodiment of the ear apparatus of the present disclosure used for heating.

In another variant, the micro-fan assembly is replaced or supplemented with a Peltier effect device. In one implementation, the Peltier effect device includes a junction which produces a cooling effect that allows for selective temperature control of at least portions of the ear canal.

In another variant, a miniature resistive heating coil is disposed proximate the micro-fan so as to enable (comparatively) warmer air to be circulated within the wearer's ear canal.

In yet a further variant, the ear apparatus includes an endothermic chemical cooling agent which utilizes an endothermic reaction to reduce the temperature of at least a portion of the ear canal. In another variant, the ear apparatus includes an exothermic chemical heating agent which utilizes an exothermic reaction to increase the temperature of at least a portion of the ear canal.

In one variant, the ear apparatus is configured to be reused indefinitely. In another variant, it is configured to be reused for only a limited number of times. In yet another variant, the apparatus is configured to be used as a disposable (e.g., single use).

Figure 7:
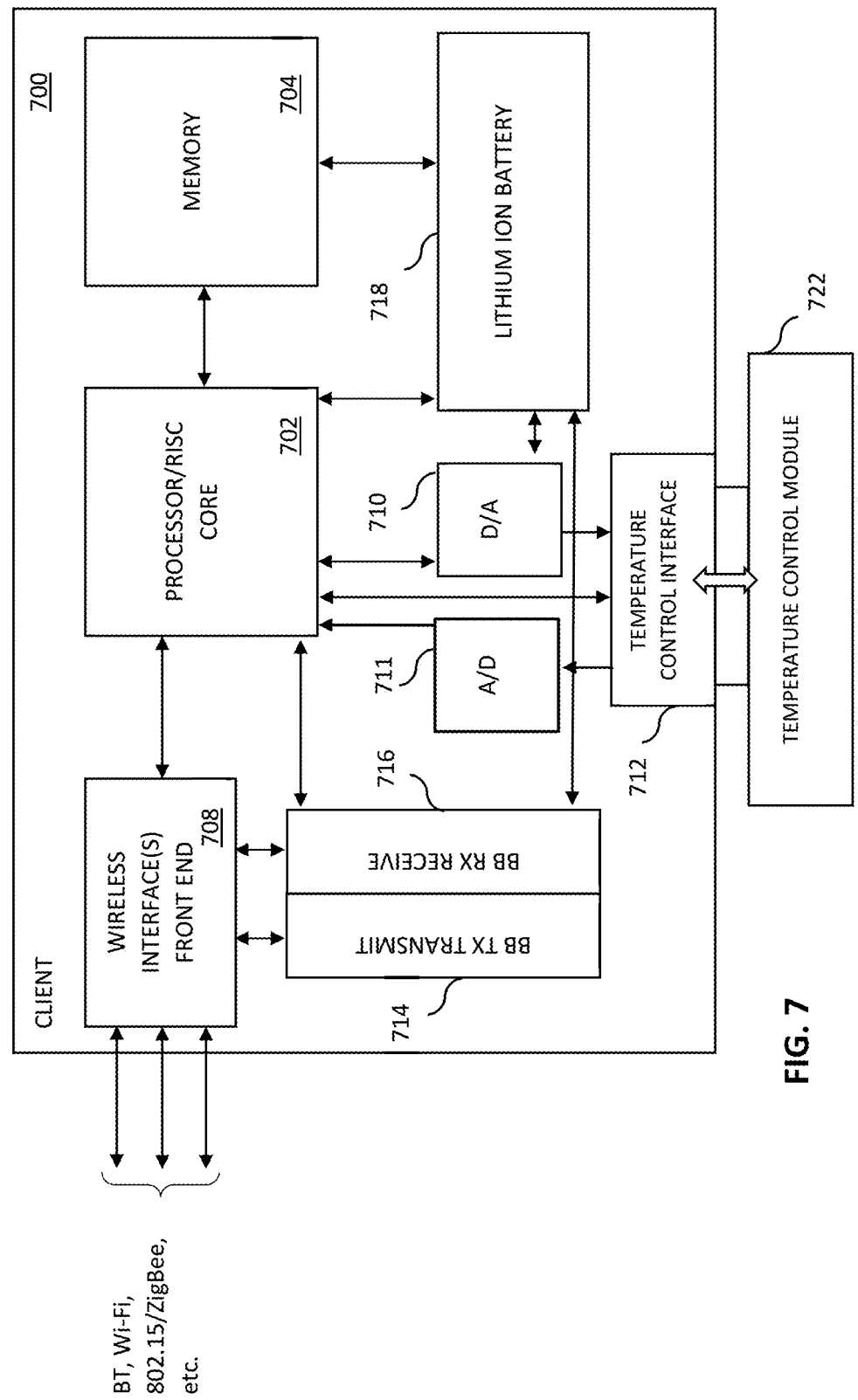
FIG. 7 is a functional block diagram of one embodiment of an electronic device according to the present disclosure.

FIG. 7 is a functional block diagram of one embodiment of an electronic apparatus adapted to implement caloric effect control according to the present disclosure. In one embodiment, the electronic apparatus is included within an at least partly compliant (e.g., elastomeric) outer body, and an interior cavity configured to contain a plurality of electronic components, although the device may also be extra-aural (i.e., implemented on an external device such as a user's smartphone, a separate standalone device, integrated with the user's clothing, part of apparel (e.g., wrist watch or smartwatch, hair braid/clip, glasses, jewelry, etc.), or other form factor.

FIG. 7 illustrates a block diagram of one such apparatus 700 according to the present disclosure. As shown, the apparatus 700 includes, inter alia, a processor subsystem 702, a memory module 704, a power supply (e.g., Lithium ion battery) 718, a digital to analog (D/A) converter 710; a temperature control interface module 712, an analog-to-digital (A/D) converter 711, one or more radio frequency (RF) front ends 708, a transmit module 714, and a receive module 716.

In one exemplary embodiment, the processor apparatus 702 may include one or more of a digital signal processor, microprocessor, field-programmable gate array, or plurality of processing components mounted on one or more substrates (e.g., printed circuit board). The processor subsystem 702 may also comprise an internal cache memory. The processor subsystem is in communication with a memory subsystem 704, the latter including memory which may for example comprise SRAM, flash, and/or SDRAM components. The memory subsystem may implement one or more of DMA-type hardware, so as to facilitate data accesses as is well known in the art. The memory subsystem of the exemplary embodiment contains computer-executable instructions which are executable by the processor subsystem.

In this and various embodiments, the processor subsystem 702 is configured to execute at least one computer program stored in memory 704 (e.g., a non-transitory computer readable storage medium). The computer program may include a plurality of computer readable instructions configured to perform various functions; e.g., data logging, profile or model generation, PID or other feedback loop control implementation, decryption, data compression (e.g., via code excited linear prediction, LPC, or other such technique), as well as operations relating to the baseband of the wireless interface(s).

In one variant, the wireless transceiver includes a Bluetooth transceiver. The temperature interface 712 in one implementation comprises a data interface such as an I2C or other low bitrate interface with associated communication protocol which in one variant communicates with the temperature control mechanism (i.e., the caloric heating/cooling circuit, which may be a fan, coil, expanding gas, endothermic or exothermic chemical, etc. as previously described in the various embodiments). A wireless interface (whether BLE, NFC, or other) may also be utilized to effect data communication between the electronic (host) 700 and the thermal control module 722.

In one approach, this interface 712 is common across a variety of different thermal control "packages" such that the electronic device 700 or "brains" of the apparatus can be interchanged onto different thermal control units, such as where the user desires to try different ones, or one type is more suited than others for that particular individual and/or ear. Data may be passed over the interface bi-directionally, such as where control signals are sent from the electronic device 700 to implement a test or profiling regime, or to the electronic device such as for temperature or other data logging based on data generated by the thermal control module 722. A micro (e.g., small disc-shape, or flat planar and flexible) lithium ion battery 1318 is included in the cavity to power the electronic components and audio output. The battery can be recharged inductively, thereby obviating exposed electrical terminals. See e.g., http://www.powerstream.com/thin-lithium-ion.htm, the contents of such website incorporated herein by reference in their entirety.

In another variant, the electronic components include a Wi-Fi transceiver (e.g., Wi-Fi or Wi-Fi "Direct" enabled) as part of the radio frequency front-end 708 and supporting components. It will be appreciated that Wi-Fi (and Bluetooth) radio transceiver integrated circuits have, as of the date of this filing, been commoditized to the extent that they are each readily available for less than one U.S. Dollar, ($1), thereby enabling their employment in limited-use or even disposable items such as ear "plugs" or apparatus as described herein.

In one variant, the Wi-Fi transceiver is configured to modulate its transmission power within the frequency band of interest to communicate only with very nearby Wi-Fi enabled devices (e.g., the user's smartphone or tablet when in their immediate possession or jacket pocket), so as to mitigate electromagnetic radiation (EMR) does to the wearer when in use. Notable, Bluetooth operating at e.g., 2.4 GHz does not suffer similar disabilities as traditional Wi-Fi transceivers, the latter designed to transmit over significantly greater ranges (i.e., WLAN vs. PAN).

In a further variant, an IEEE Std. 802.15 PAN-enabled integrated circuit device (e.g., Zigbee® or the like) is utilized within the cavity. Similar to the aforementioned 802.11 and Bluetooth wireless devices, ZigBee-enabled devices are generally commoditized, short-range devices capable of lower-bandwidth communications with nearby devices, such as a user's mobile device (e.g., smartphone or personal media device), PAN access nodes, etc. for at least one-way communication with the ear apparatus.

In another variant, the electronic apparatus is configured as a selectively actuated ear device, and the apparatus acts as one or more "IoT" ("Internet of things") entities. For instance, the user's ear apparatus can be configured to communicate with wireless home or premises automation apparatus, such as to activate the ear apparatus within the home or premises upon occurrence of an event (e.g., the user "turning the home on" such as after arriving from work), or detection of other IoT-related device events (e.g., lights being turned on in a particular room, thereby ostensibly indicating the user's presence, or the stove being turned on, thereby indicating the user cooking dinner, or the spa being turned on, thereby indicating the user soaking therein). For instance, the stove or oven being turned on, or the refrigerator door being opened, or a portable lighter being sparked, may cause the caloric effect apparatus to be actuated to mitigate the user's hunger, desire for alcohol, cigarettes, etc. immediately preceding or during the event.

In yet a further variant, the cavity includes a miniature accelerometer in signal communication with a processor or microcontroller integrated circuit (e.g., ASIC). In one implementation, the accelerometer is used to sense the state of the wearer of the ear apparatus; e.g., ambulatory, awake but non-ambulatory, or asleep/unconscious. Such state determination can be used for e.g., gating of one or more functions of the ear apparatus, such as where caloric effect control of the ear apparatus (and/or transmission from the ear apparatus, such as via the aforementioned biometric or telemetry signals such as temperature, heart rate, ambulatory status, etc.) is only enabled when the user is ambulatory or waking/non-ambulatory. Exemplary MEMS-based micro-accelerometer apparatus useful with the present disclosure are described in, e.g., U.S. Patent Application Pub. No. 20130247669 to Swanson, et al. published Sep. 26, 2013 and entitled "Apparatus and Method for Providing an In-Plane Inertial Device with Integrated Clock", and Patent Application Pub. No. 20140062567 to Waters, et al. published Mar. 6, 2014 and entitled "Auto-Ranging for Time Domain Extraction of Perturbations to Sinusoidal Oscillation", each of the foregoing incorporated herein by reference in its entirety, although it will be appreciated that the foregoing accelerometers are merely exemplary, and other types and/or configurations may be used consistent with the ear apparatus of the present disclosure.

In yet another embodiment (see FIG. 7a), a so-called "skill" platform 722, 724 such as the ubiquitous Amazon Alexa® platform may be used consistent with the disclosed apparatus for, inter alia, control of the ear apparatus 700. For example, using the Amazon AWS development platform, a skill can be readily developed for the user's client device (e.g., Amazon Echo, Dot, or similar)722 such that the user can speak to the client device in normal conversation tone, including "wake" or hot word(s) for activation, and cause the ear apparatus to implement one or more commands (e.g., invoke a control regime or test program, or other function). Various API (application programming interface) functions may be defined for the apparatus (akin to existing Echo/Dot APIs for e.g., audio, etc.) such that the ear apparatus 700 can be controlled wirelessly in its varying functions, as dictated by specific verbal constructs (e.g., certain user-specific phrases can be defined which can be correlated to certain intent(s) and subsequently invoke certain prescribed actions).

In this capacity, the ear apparatus 700, as controlled via its indigenous PAN or WLAN interface as previously described when in data communication with the Alexa-enabled client 722 (or a proxy device thereof, such as a gateway in wireless or networked (wireline) connectivity with the client device), implements various functions at the user's verbal request (e.g., "Alexa, start John Q. Public no-smoking therapy routine Number 1—left ear"). Such functions might include e.g., starting/stopping therapy or testing, increasing/decreasing caloric stimulation (e.g., increase air flow to the ear under treatment), invoking a user-specific therapy profile (including ones that may be ear- or side-specific for some users), causing the access of one or more networked devices 728 (including via the Internet backhaul of the premises where the user is located) to obtain data of relevance such as prior therapy treatment data, data relating to Deep Learning (DL) or Artificial Intelligence (AI) or other machine learning algorithms relating to data generated for the user (or more broadly a population of different users).

Figure 7A:
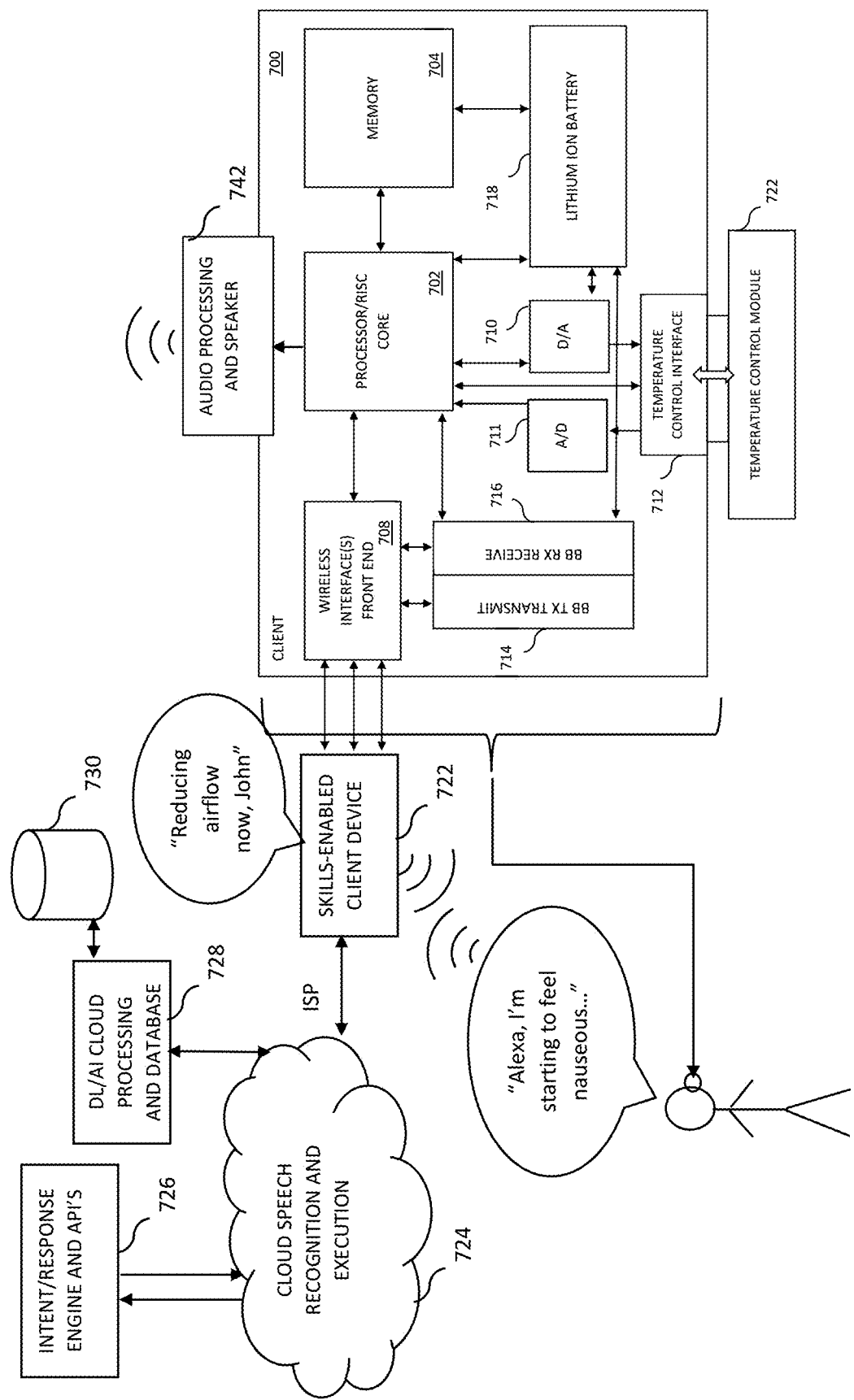
FIG. 7a is a functional block diagram of another embodiment of an electronic device and associated cloud processing platform(s) according to the present disclosure.

In one configuration of the ear apparatus, a miniature "ear bud" or speaker 742 is also included within the apparatus such that audio feedback or information can be passed to the user while the therapy session is underway (or prior/after). Likewise, the aforementioned skill platform can be used to receive user input or feedback e.g., during a therapy session (also as shown in FIG. 7a), which can then be used: (i) to provide audible feedback "aloud" (versus use of an installed apparatus microphone), and (ii) as the basis of a control loop for the ear apparatus 700, such as to wirelessly command it to reduce airflow, start/stop, etc. The former approach has the advantages of privacy and non-interruption of other persons via audible emissions of the skill-enabled client.

It will also be appreciated that the exemplary cloud-based DL/AI platform 728 shown in FIG. 7a may be utilized for example to enhance the performance of the user's individual ear apparatus, or subsets of a population of users. For example, in one embodiment, data gathered during invocation of one or more therapy or testing sessions for a given user may be uploaded to the cloud platform (e.g., DL/AI server or proxy thereof) for use and analysis via DL or AI algorithms. Data from multiple different ear apparatus users can similarly be uploaded and stored such as in the database 730. Physical or demographic data such as user's sex, age, race, weight, height, afflictions, medications/dosage, and similar can also be associated with the uploaded data (whether uploaded concurrently, or accessed via another database such as that of a medical service provider).

In one implementation, all such data is anonymized (e.g., using a one-way cryptographic hash or other cryptographic mechanism for generating a non-reversible unique identifier for each user/data set), such that privacy obligations are observed, and the data even if breached cannot be traced back to any particular individual. The same hash function can be used on initial data upload or submission (e.g., a user's personal and demographic data) as well as therapy session results or feedback, thereby allowing correlation of the data sets while still maintaining anonymity.

Such DL and AI algorithms may, when used to process the data set of interest (whether belonging to just the particular user, such as where multiple therapy sessions and results are analyzed, or more broadly to larger populations of users) provide the ear devices 700 with useful and customized control algorithms based on observations or behaviors/responses gleaned from the DL/AI processing. For example, a subset of the population comprising Caucasian men between ages 40 and 55 may exhibit (such as on a mean/median or other statistical basis) certain commonalities in their response to certain levels (e.g., temperatures) and durations of applied therapy, whereas Asian females aged 20-40 might have a markedly different response. As such, user-specific and "class" or "category" specific therapy profiles can be generated for use, at least as a starting point for users falling within the respective categories. Thereafter, the DL/AI engine analytics may refine the profile or therapy regime for a given individual based on their particular responses, in effect performing cloud-based "fine tuning" of the therapy regimes for each individual (or class of individuals) as more data is gathered via e.g., upload to the cloud.

It will be appreciated that the DL/AI interface and associated APIs may be integrated with the functionality of the skills-enabled client 722 as shown in FIG. 7a (e.g., the cloud function 724 supporting speech recognition and intent determination and response generation, can also make API "calls" to the DL/AI server for processing of user data), or the DL/AI service may operate independently.

As one example of the foregoing, a user may say "Alexa, generate a no-smoking therapy routine for John Q. Public", at which point the intent APIs and engine within the cloud SR and intent processing logic 724 will access the intent engine 726 (FIG. 7a) to determine that the user desires generation of a new non-smoking routine specifically adapted to them. The logic of the platform 724 may be configured to execute this intent by first making an API call to the DL/AI platform 728, using the user's personal data (anonymized) as a search or entry point. As such the DL/AI modeling and analytics can take the user-specific data (e.g., male Caucasian 50-55 who has been smoking for 10 years) to run DL/AI models to generate a "starting" therapy regime for the user, such as where the user places the apparatus in their left ear, the apparatus starts with a "training" regime to determine user response (which can be fed back manually or verbally by the user, or even detected such as via REM data generated via a REM sensor affixed to a user's eyeglasses or a VR headset). Based on the response, the therapy regime is adjusted or calibrated (e.g., via another API call to the cloud DL/AI platform), and the updated therapy regime loaded onto the ear apparatus 700 for execution. By accessing data for many similarly situated users of similar devices (e.g., how they respond to certain stimuli, the efficacy of the therapy, etc.), the DL/AI models can adaptively "learn" to recognize (i) constructs or patterns of certain types of user behaviors (e.g., ramping thermal stimulus too rapidly on certain individuals or classes of individual can result in an unwanted "nausea excursion," or too little stimulus provides effectively no therapeutic benefit, or one ear on certain individuals has a markedly different response than the other ear on the same individual), (ii) certain types of markers for success of the therapy, (iii) certain types of failure events or degradations of the ear apparatus 700 or its use (e.g., device component failure, device becoming dislodged or not inserted far enough into the ear, user swimming or showering with device, etc.), and (iv) certain use or application contexts for the apparatus (e.g., user sleeping or user ambulatory based on e.g., accelerometer data, user jogging or running, user being outdoors in cold or hot weather, etc.).

Moreover, familial or other relationships may be leveraged in the DL/AI analyses (or otherwise). For instance, where data from several related family members is available, certain common characteristics, responses, physiological anomalies, etc. may be present and identified, and used to better construct or adapt the therapy regime(s) applied to one or more of the members. Genetically, family members may share a number of commonalities which may express themselves as common behaviors, responses, or similar factors that can be detected via e.g., DL or AI analysis.

Figure 10:
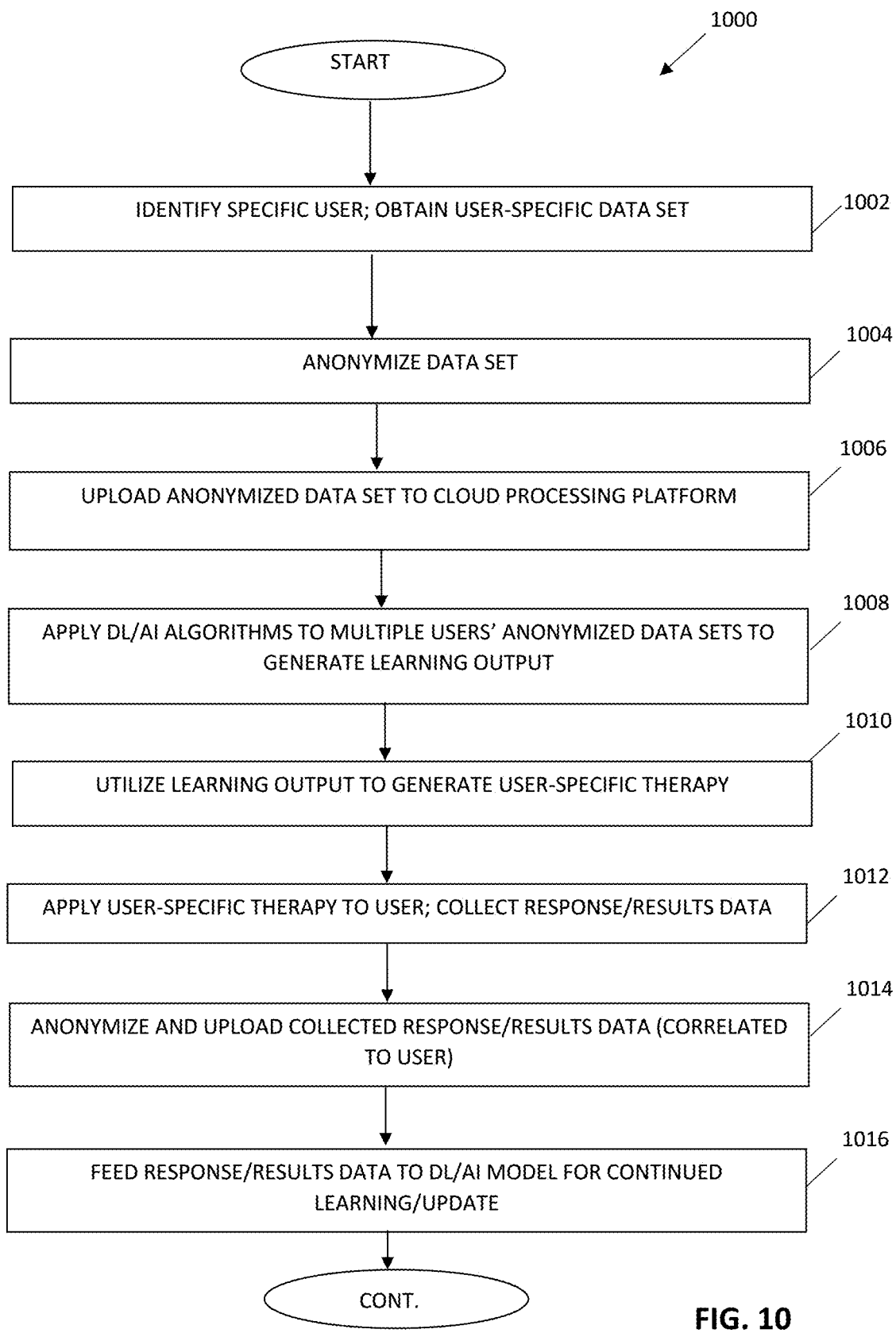
FIG. 10 is a logical flow diagram of an exemplary method of data processing and analysis according to the present disclosure.

Steps 1002 through 1016 of the method 1000 of FIG. 10 illustrate one embodiment of the foregoing logic which can be used to process data relating to individual users for subsequent (and iterative, where desired) processing of therapy session results, according to the disclosure.

Methods

Figure 8:
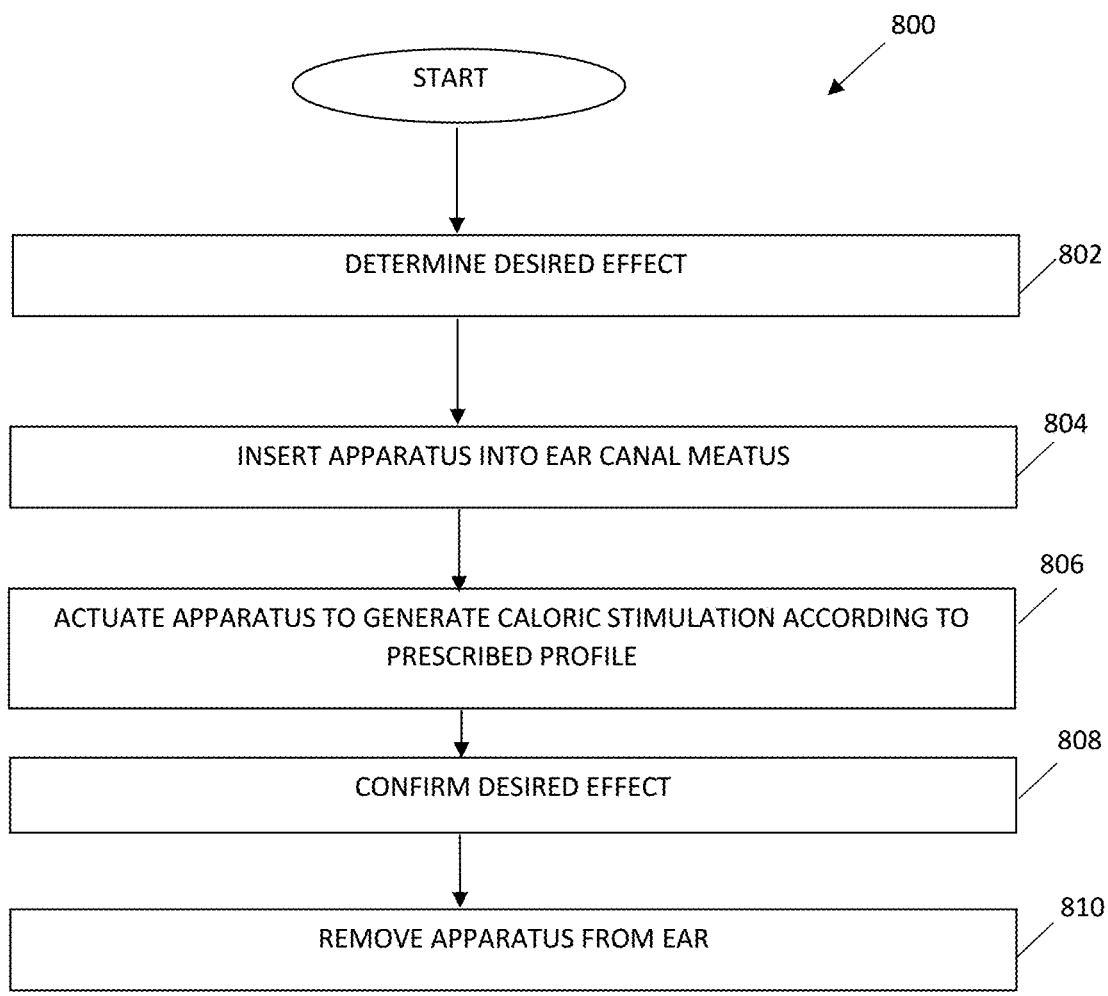
FIG. 8 is a logical flow diagram of an exemplary method of use of a selectively controlling user behavior according to the present disclosure.

FIG. 8 is a logical flow diagram of an exemplary method of use of a selectively controlling user behavior according to the present disclosure. As shown, the method 800 includes steps 802-810 which involve determining the desired response or effect, inserting the apparatus into the target ear canal, actuating the apparatus to generate caloric stimulation, confirming the desired effect, and removing the apparatus from the ear afterwards. According to one example implementation of the method (appetite suppression), the following procedure is used:

1. 15 minutes to half hour before eating, cool the ear of the subject for a duration previously calibrated to the specific individual (see discussion below) to induce feelings of satiation/suppression;
2. The satiety effect suppresses appetite or other urges in the lag period which occurs after ingestion but prior to the natural post prandial satiation which occurs when nutrient levels increase in the subject's circulatory system.
3. Use: repeat daily or more often as needed.

Accordingly, the foregoing results in reduced caloric intake by the user, enhanced portion control and hence weight loss over time. It is noted that potential side effects may result if the dosing time is abused, such as e.g., vertigo could be induced as an unwanted but not harmful side effect. Moreover, discomfort relating to the position of the unit inside the ear could occur in some cases; from outer to inner, about ⅔ of the ear canal is cartilage behind skin. Closer to the eardrum, the remaining approximately ⅓ of the canal is bone just inside the skin. When a cold medium (e.g., balloon element) touches the skin over the bony portion, it may be painful to some subjects, but if the (example) balloon contacts the outer ⅔ of the canal, the discomfort is typically far less. Hence, the present disclosure contemplates that proper placement for each individual may vary, but improper placement can have adverse consequences to varying degrees for each individual and as such, a "spatial" characterization of each ear canal in terms of thermal sensitivity, user pain or discomfort experienced, degree of efficacy of the caloric stimulation on the target behavior, etc. may be useful.

In another aspect, a method of characterizing a user in terms of caloric effect response is disclosed. In one embodiment (FIG. 9), the method 900 includes steps 902-912 which include selection of a target or testing ear, inserting a selectively controllable caloric apparatus into the user's ear canal, and invoking various stimuli (increase and decrease in temperature for varying periods of time) according to a test regime or plan, and observing or recording the user's reaction(s) to the various stimuli. From this data, an optimized user-specific profile may be generated, which may also vary from one ear to the other on a given user (e.g., ear-specific profiles may be generated and utilized by the apparatus during subsequent operation).

Figure 9:
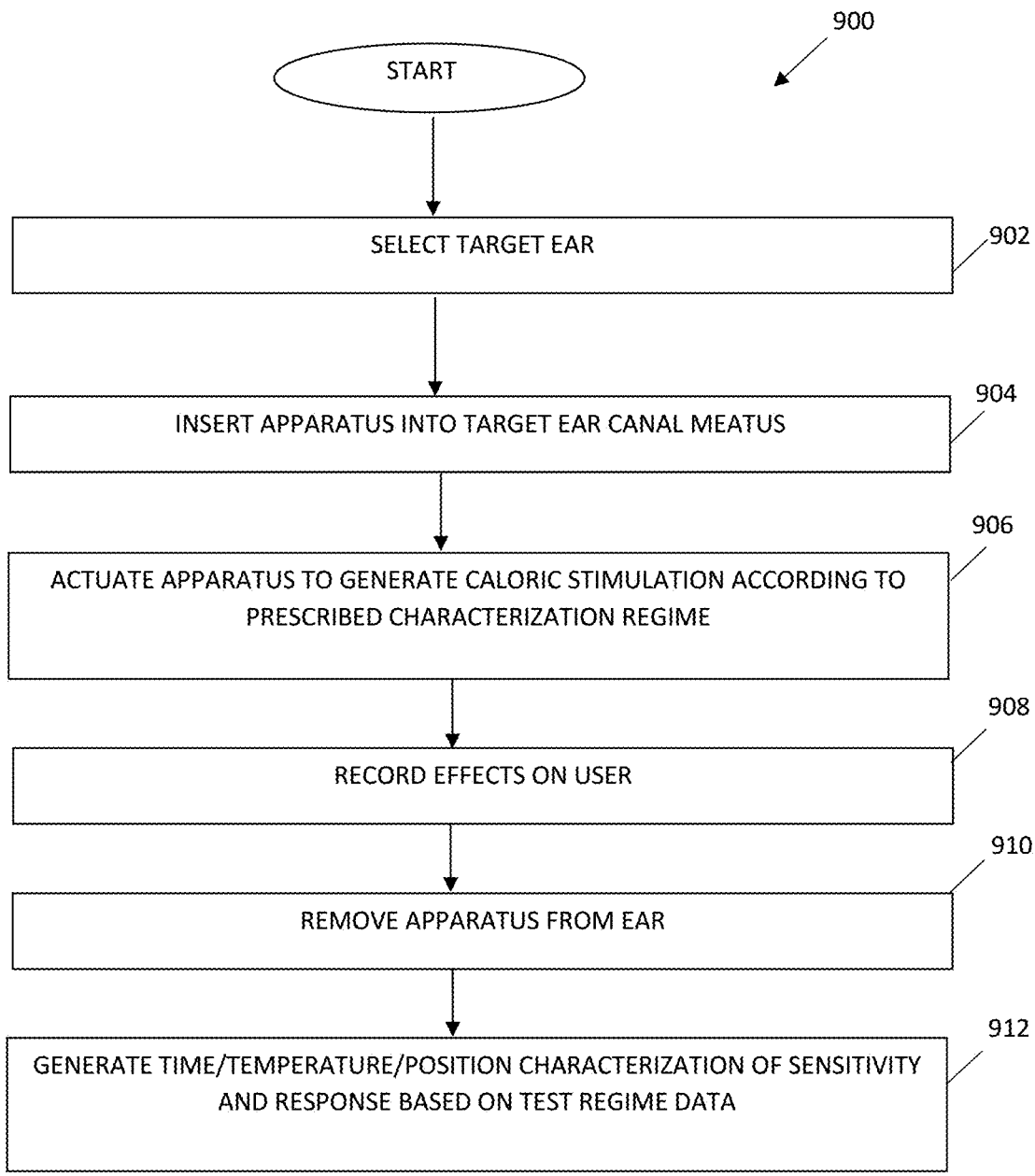
FIG. 9 is a logical flow diagram of an exemplary method of use of a selectively characterizing ear canal response and user behavior according to the present disclosure.

Note also that the methodology of FIG. 9 may be used with respect to observed/detected REM as a basis of calibration of a specific individual. For example, as noted above, each individual's response may vary based on their physiology and/or other factors, and hence accurate characterization of response in terms of when the "sweet spot" or target level of REM is achieved can be used as a basis for calibrating the therapy for each individual.

As previously noted, one effect of the caloric stimulation described herein with respect to the exemplary embodiments is rapid eye movement (REM). Such REM generally starts at a slow frequency, and accelerates as the duration of the stimulation is lengthened. Moreover, the longer that the stimulation is applied, the more/more intense the resulting nausea that the subject feels. In anecdotal testing provided by the inventors hereof, after about 4-5 minutes (utilizing ice water as a stimulation medium), the subject has been observed to feel as if they have a terrible sea-sickness. This longer duration accordingly may be used to alter more addictive behaviors.

Additionally, it is noted that based on such anecdotal testing, the temperature at which onset of the aforementioned caloric reflex occurs is on the order of 7° C. (about 12.6° F.) above or below the nominal human body temperature of 37° C. (98.6° F.). Hence advantageously, such magnitude of stimulus is (i) well within tolerable limits of the average human, even if highly sensitive tissue such as that of the ear canal is utilized, and (ii) easily achieved even with small amounts of stimulus media (e.g., cold water, warm water, exothermic or endothermic chemicals, resistive heaters, Peltier-effect coolers, etc.), thereby allowing for smaller, more mobile (and even disposable) implementations of the therapy apparatus.

It is further noted that as observed by the inventors hereof, a temperature gradient between the user's two ears is in some cases necessary in order to achieve the desired effect(s) on behavior modification. While the origins of such gradient may be from (i) cooling one ear relative to the other; (ii) heating one ear relative to the other, (iii) cooling one ear relative to a nominal temperature, and heating the other ear relative to the nominal, or (iii) heating/cooling one ear relative to a nominal temperature, and heating/cooling the other ear relative to the nominal except to a lesser or greater magnitude than the first ear, the presence of the gradient has been observed to invoke the responses described above. While from a practical standpoint, applying stimulus to one ear only is often more simple and efficient, the present disclosure contemplates cases or applications where application of stimuli according to one of the "two ear" models above is useful, especially since a given absolute magnitude of the gradient between the ears can be achieved by smaller relative changes in each ear in some cases. For instance, cooling one ear by a value of X° and heating the other ear by Y°, where X+Y=the total desired magnitude of the temperature change for stimulus to be effective (which may or may not be the above-mentioned 7° C., due to differential effects), results in a smaller temperature excursion or stimulus to each ear as compared to the case where one ear was used alone.

Figure 11:
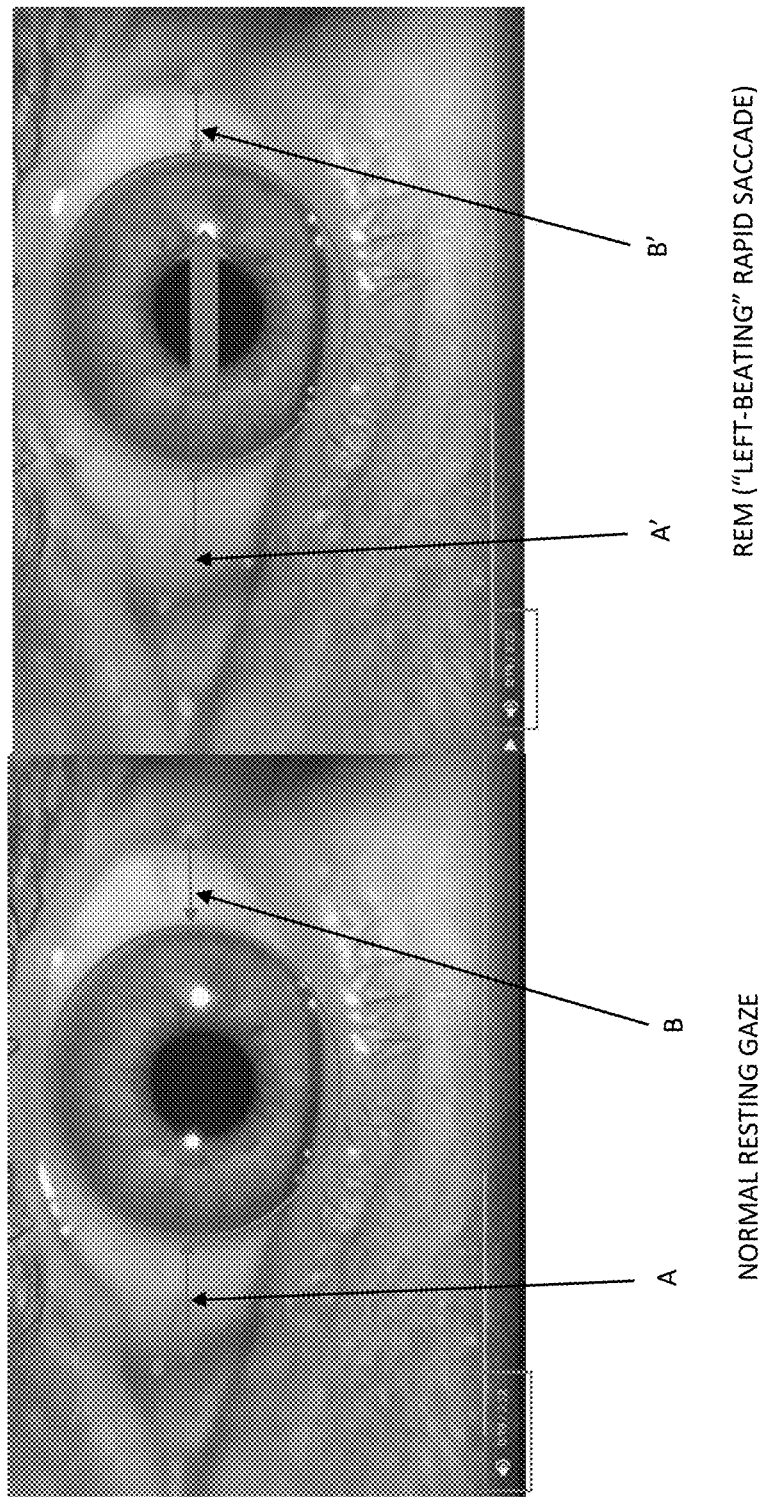
FIG. 11 is a pictorial representation of an actual subject's eye twitch or REM during caloric stimulation during testing conducted by the inventors hereof.

Referring now to FIG. 11, an actual test of the methodology and apparatus described herein is shown. In exemplary implementations, the point when the subject's eye(s) begin to perceptibly twitch (e.g., a rotation of the subject's eyeball on the order of a few degrees such that it can be visually perceived, including in some cases where the eyelid is closed and the underlying "twitch" can be seen via movement of the eyelid itself) is correlated to a feeling of mild "queasiness" in the subject, without any significant nausea. As shown in FIG. 11, within the space of a fraction of a second, the test subject's eyeball involuntarily twitches to the right (their left) a few degrees, and then back again. This point of the therapy (i.e., detectable REM or twitching) is significant for, inter alia, hunger satiation/suppression, since it is a readily ascertainable event, and is also a boundary for further (more severe) aversion stimulus equating to a greater feeling of nausea. As such, exemplary embodiments of the apparatus and methods described herein make use of this observation in determining the duration of stimulus to apply. For example, apparatus such as that disclosed in U.S. Pat. No. 9,271,648 to Durnell, et al. issued Mar. 1, 2016 entitled "Eye tracking apparatus," incorporated herein by reference in its entirety, may be used consistent with the present disclosure to enable user/wearer eye position and movement concurrent with use of goggles, glasses, or other vision apparatus.

In one variant, a user's smartphone is configured to run an application program installed thereon, the application program configured to evaluate one or more characteristics (such as direction of gaze, retinal location, etc.) related to the user's eye via the smartphone's indigenous CMOS/CCD camera capabilities. See, e.g., http://www.umoove.me/, regarding. Umoove software-only face and eye tracking technology, ostensibly built especially to facilitate the challenges in mobile environments such as shakiness, lighting and limited hardware resources. The manufacturer indicates that this technology runs at a CPU as low as 5% in real-time and needs nothing but the raw frames of the front-facing camera for input. Further included is an interpretation layer which turns the face and eye movements into a language of interaction and data which may be utilized for implementing the methodologies described herein; i.e., as input to algorithms executing on that same smartphone, or a cloud-based entity in communication with the smartphone or other platform which can provide either active control or passive feedback as to continued/level of stimuli to be applied to the user during behavior modification therapy. For instance, in one exemplary active control or feedback scenario, the apparatus 700 of FIG. 7 or 7a is used to control the operation of a temperature control module 722, based on signals received wirelessly via the BLE/BT/802.15.4/ZigBee, etc. interface 708 thereof from a corresponding BLE/BT/802.15.4/ZigBee, etc. transceiver on the user's smartphone or portable, the latter running the aforementioned algorithm to detect REM. The user merely holds the smartphone up to their eye, and the app executes to provide data to the module 700 to modulate (on/off, vary magnitude) the caloric stimulus applied. In a "passive" implementation, the user uses the same app/portable, but instead of the app and smartphone passing control data to a module 700, the app may simply emit an audible tone, screen display, haptic output, etc. to alert the user that it is time to remove/stop the caloric stimulus (e.g., manually, such as by removing the crushable ampule or ear insert, etc. presently applying the stimulus).

Notably, the exemplary Umoove is packaged as three SDKs; Face SDK, EyeMovement SDK and objectTracking SDK, all of which are available for iOS and Android, and hence may be broadly utilized for development of the aforementioned application program when properly configured via the appropriate SDK(s), such configuration within the skill of ordinary artisan when given the present disclosure. See also the Samsung Galaxy S9 and S9+ in relation to retinal recognition and registration capabilities.

Moreover, in less sophisticated embodiments, an eye/retina tracking algorithm without motion/jitter compensation can be used consistent with a supporting structure (e.g., glasses or goggles configured to receive and hold the user's smartphone in proper position such that the aforementioned tracking can be conducted reliably). Such other apparatus including Google Glass or similar may also be adapted for such purposes (i.e., using its indigenous optical elements modified to enable retinal/eye position scan and use this as input to the aforementioned application running on e.g., a Bluetooth or BLE connected smartphone or other portable. Desktop/laptop computer variants are also envisaged herein (e.g., using each's web camera capabilities).

FIG. 12 is a tabular representation showing exemplary test results obtained by the inventors hereof using a prototype ear apparatus for caloric effect control of appetite suppression.

Hysteresis

In a further aspect, a method of treating a patient with behavioral condition or deficiency is disclosed. In one embodiment, the method includes installing a selectively variable or controllable apparatus within the ear canal; adjusting at least one aspect of the apparatus so as to permit a desired amount of air and/or other medium into the canal during normal wear; and monitoring the effect on the patient being treated to determine or identify a desired effect thereon.

It will also be recognized that, based on the particular type of stimulus introduced (e.g., relative heat or cold), the longevity of the stimulus, the rate at which the stimulus is introduced or "ramped," and/or other such factors, a given living being may experience a hysteresis type of effect. For example, in some cases, a being to which a given therapy has been applied may, upon subsequent application of the same therapy profile within a short period of time, experience less or more of an effect, and/or somewhat different effects. For instance, if a cold therapy regimen is applied at time T, then at t=T+N minutes, application of the same regimen may produce either mitigated or exacerbated effect relative to the first regime, based on the particular individual. Such hysteresis effects may even occur "cross-ear", i.e., where a therapy regimen applied to a first ear produces a first effect, and the same regimen applied to the other (previously untreated) ear may produce different effects, including depending on the temporal proximity of the two therapy applications.

As such, the various methods, algorithms, and DL/AI analytic approaches described herein may be readily adapted by those of ordinary skill when given this disclosure so as to account for such observed or known (or hypothecated) hysteresis effects. For example, in cases where a given regimen is applied, and must be successively used again in a reasonably short period of time, the parameters of the regimen (e.g., time/temperature profile) may be adjusted to account for the hysteresis, such as by extending the temporal profile for a given application of temperature, increasing/reducing the temperature relative to the prior session, and so forth, so as to reach the desired "cumulative" effect of the two (or more) therapy sessions on the subject. User-specific (and class/type specific) hysteresis profiles are accordingly contemplated herein, such as those based on prior observed responses of the user or those similar in physiologic attributes or other identified parameters or relevance. For example, the aforementioned DL/AI modeling and analytics may converge on a prescribed hysteresis correction factor, function, or table that can be applied based on DL/AI output (e.g., Caucasian males aged 40-55 generally exhibit a decaying exponential loss of sensitivity or efficacy of a given thermal profile as a function of time).

Additional Considerations

It will be recognized that while certain aspects of the disclosure are described in terms of a specific sequence of steps of a method, these descriptions are only illustrative of the broader methods of the disclosure, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the disclosure disclosed and claimed herein.

While the above detailed description has shown, described, and pointed out novel features of the disclosure as applied to various embodiments, it will be understood that various omissions, substitutions, and changes in the form and details of the device or process illustrated may be made by those skilled in the art without departing from the disclosure. This description is in no way meant to be limiting, but rather should be taken as illustrative of the general principles of the disclosure. The scope of the disclosure should be determined with reference to the claims.

It will be further appreciated that while certain steps and aspects of the various methods and apparatus described herein may be performed by a human being, certain of the disclosed aspects and individual methods and apparatus are generally computerized/computer-implemented. Computerized apparatus and methods are necessary to fully implement these aspects for any number of reasons including, without limitation, commercial viability, practicality, and even feasibility (i.e., certain steps/processes simply cannot be performed by a human being in any viable fashion).

What is claimed is:

1. Therapy apparatus, comprising:
a first element configured to fit within at least a portion of an ear of a living subject, the first element comprising a thermal control apparatus configured to selectively perform at least one of increasing or decreasing temperature of at least a portion of an ear canal of the living subject to effect behavior modification thereof;
wherein the thermal control apparatus comprises a compressed gas apparatus configured to selectively release portions of a volume of a compressed gas within the ear canal, the selective release causing absorption of thermal energy in the ear canal.

2. The therapy apparatus of claim 1, further comprising apparatus configured to detect REM (rapid eye movements) of the living subject in response to the selective performance of the at least one of the increasing or the decreasing of the temperature of at least the portion of the ear canal, and generate at least one of signals or data relating to the detected REM.

3. The therapy apparatus of claim 2, wherein the thermal control apparatus is configured to receive and utilize the generated at least one of the signals or the data relating to the detected REM in order to control at least one aspect of the selective performance of the at least one of increasing or decreasing of the temperature.

4. The therapy apparatus of claim 1, further comprising wireless interface apparatus in data communication with the thermal control apparatus, the wireless interface apparatus configured to at least wirelessly receive data corresponding to one or more commands to be implemented by computerized logic of the thermal control apparatus, the one or more commands relating to the selective performance of the at least one of the increasing or the decreasing of the temperature.

5. The therapy apparatus of claim 4, wherein the one or more commands to be implemented by the computerized logic of the thermal control apparatus are received from a computerized apparatus (i) having a second wireless interface configured to communicate with the wireless interface apparatus of the therapy apparatus, and (ii) which has received user-provided feedback on one or more aspects of a then-current ongoing therapy session.

6. The therapy apparatus of claim 1, further comprising wireless interface apparatus in data communication with the thermal control apparatus, the wireless interface apparatus configured to at least wirelessly transact data corresponding to one or more time-stimulus profiles to be implemented by the thermal control apparatus during the selective performance of the at least one of the increasing or the decreasing of the temperature.

7. Computer readable apparatus comprising a non-transitory storage medium, the non-transitory storage medium comprising at least one computer program having a plurality of instructions, the plurality of instructions configured to, when executed on a processing apparatus, cause a therapy apparatus to:
cause a first element of the therapy apparatus to fit within at least a portion of an ear of a living subject;
configure a thermal control apparatus to selectively perform at least one of an increase or decrease in temperature of at least a portion of an ear canal of the living subject to effect behavior modification of the living subject;
receive input via a graphical user interface generated on a display device of the therapy apparatus, the input indicating at least a change in frequency of rapid eye movement (REM), the change in the frequency of the REM relating to at least one of a type or severity of a physiologic response felt by the living subject during application of at least one of a predetermined routine or predetermined regimen of the at least one of the increase or the decrease in the temperature; and
utilize the input to generate data to modify at least one of a duration or magnitude of the at least one of the predetermined routine or the predetermined regimen, to obtain an optimized level of a desired physiologic effect on the living being.

8. The computer readable apparatus of claim 7, wherein the configuration of the thermal control apparatus to selectively perform the at least one of the increase or the decrease in the temperature comprises use of a valve assembly to modulate an amount of fluidic medium within the first element and which enters the ear canal from an exterior environment so as to control one or more behaviors of the living subject.

9. A method for utilizing a therapy apparatus to effect a behavior modification, the method comprising:
inserting a first element of the therapy apparatus into an ear canal of a living subject;
causing, via a thermal control apparatus of the first element, at least one of an increase or decrease in temperature of at least a portion of the ear canal of the living subject to effect the behavior modification thereof;
receiving feedback data, the feedback data indicating at least a change in frequency of rapid eye movement (REM), the change in the frequency of the REM relating to at least one of a type or severity of a physiologic response felt by the living subject during application of at least one of a predetermined routine or regimen of the at least one of the increase or the decrease in the temperature; and
utilizing the feedback data to generate data to modify at least one of a duration or magnitude of the at least one of the predetermined routine or the regimen to obtain an optimized level of a desired physiologic effect on the living subject.

10. The method of claim 9, wherein:
the causing of the at least one of the increase or the decrease in the temperature comprises causing the at least one of the increase or the decrease in the temperature for varying periods of time; and
the method further comprises recording data relating to one or more reactions of the living being to the at least one of the increase or the decrease in the temperature over the varying periods of time, the data comprising the feedback data.

11. The method of claim 10, further comprising:
generating, based on the data relating to the one or more reactions, a time-and-temperature user-specific profile; and
causing adjustment of the time-and-temperature user-specific profile according to a hysteresis correction function.

12. The method of claim 9, further comprising causing the first element to have a prescribed degree of conformance to tissue of the ear canal, the causing of the first element to have the prescribed degree of the conformance to the tissue of the ear canal comprises filling a balloon-like structure with a working medium to enable a prescribed degree of surface contact between the working medium inside the balloon-like structure and the tissue via material of the balloon-like structure, the filling of the balloon-like structure with the working medium comprises filling the balloon-like structure with a substance that is at least one of a gaseous medium or liquid medium depending on a temperature of the substance.

13. The method of claim 9, wherein the behavior modification is selected from a group consisting of: (i) mitigating a desire to smoke tobacco; (ii) mitigating a desire to drink one or more alcoholic beverages; (iii) mitigating a desire to ingest one or more pharmacological agents; and (iv) hunger satiation or suppression.

14. The method of claim 9, wherein the first element comprises an exothermic or endothermic chemical apparatus configured to give off or absorb thermal energy, respectively.

15. The method of claim 9, wherein the first element comprises an electric or electronic heater apparatus configured to give off thermal energy.

16. The method of claim 9, wherein the first element comprises an electric or electronic fan apparatus configured to create a differential pressure between the ear canal and an ambient area outside the ear canal in order to cause ingestion of air from the ambient area into the ear canal, the ingested air being at a temperature lower than a temperature of the ear canal.

17. The method of claim 9, wherein the receiving of the feedback data comprises receiving data via an application program running on a computerized mobile device, the computerized mobile device comprising a camera configured to capture the change in frequency of the REM.

* * * * *